United States Patent
Iseli et al.

(10) Patent No.: US 9,889,041 B2
(45) Date of Patent: Feb. 13, 2018

(54) DEVICE FOR A MEDICAL TREATMENT OF A SCLERA

(71) Applicants: Universitat Leipzig, Leipzig (DE); Hans Peter Iseli, Geroldswil (CH)

(72) Inventors: Hans Peter Iseli, Geroldswil (CH); Mike Francke, Leipzig (DE); Peter Wiedemann, Leipzig (DE)

(73) Assignee: UNIVERSITAT LEIPZIG, Leipzig (DE)

(*) Notice: Subject to any disclaimer, the term of this patent is extended or adjusted under 35 U.S.C. 154(b) by 67 days.

(21) Appl. No.: 14/434,045

(22) PCT Filed: Oct. 8, 2013

(86) PCT No.: PCT/EP2013/070918
§ 371 (c)(1),
(2) Date: Apr. 7, 2015

(87) PCT Pub. No.: WO2014/056895
PCT Pub. Date: Apr. 17, 2014

(65) Prior Publication Data
US 2015/0257928 A1    Sep. 17, 2015

(30) Foreign Application Priority Data
Oct. 8, 2012  (EP) .................................. 12187675

(51) Int. Cl.
*A61F 9/00* (2006.01)
*A61K 9/00* (2006.01)
(Continued)

(52) U.S. Cl.
CPC ............ *A61F 9/0017* (2013.01); *A61B 18/24* (2013.01); *A61B 2018/1807* (2013.01);
(Continued)

(58) Field of Classification Search
CPC ...... A61F 9/0079; A61F 9/0017; A61F 9/007; A61F 9/00736; A61F 9/0008;
(Continued)

(56) References Cited

U.S. PATENT DOCUMENTS 3,327,712 A * 6/1967 Kaufman ........... A61B 1/00165
348/359
5,725,493 A   3/1998 Avery et al.
(Continued)

FOREIGN PATENT DOCUMENTS

CN      1630494     6/2005
CN      102202708   9/2011
(Continued)

OTHER PUBLICATIONS

"Agent." Merriam-Webster.com. Merriam-Webster, n. d. Web. Apr. 4, 2017.*
(Continued)

*Primary Examiner* — Nathan R Price
*Assistant Examiner* — Courtney Fredrickson
(74) *Attorney, Agent, or Firm* — Kagan Binder, PLLC

(57) ABSTRACT

The invention relates to a device for a medical treatment of a sclera, the device (100) comprising a curved disc or a belt (102), wherein the disc/belt is configured to be placed into the Tenon's space; the disc/belt is formed such that the inner surface of the curved disc/belt is superficially contactable to the surface of an area of the sclera so as to superficially cover said area; and the disc/belt comprises one, two, three, four, or more independent channel systems (101).

32 Claims, 13 Drawing Sheets

(51) Int. Cl.
  *A61F 9/007* (2006.01)
  *A61M 25/00* (2006.01)
  *A61B 18/24* (2006.01)
  *A61B 18/22* (2006.01)
  *A61B 18/18* (2006.01)

(52) U.S. Cl.
  CPC ....... *A61B 2018/2261* (2013.01); *A61F 9/007* (2013.01); *A61F 9/0008* (2013.01); *A61F 9/0079* (2013.01); *A61F 9/00736* (2013.01); *A61F 2250/0067* (2013.01); *A61K 9/0051* (2013.01); *A61M 25/003* (2013.01); *A61M 25/0068* (2013.01); *A61M 2210/0612* (2013.01); *F04C 2270/041* (2013.01)

(58) Field of Classification Search
  CPC ................ A61K 9/0051; A61N 5/1017; A61N 2005/1018; A61N 2/004; A61N 5/062; A61N 2005/0635; A61N 2005/0636; A61N 2005/0637; A61N 2005/0639; A61N 2005/064; A61N 2005/0641; A61N 2005/0645; A61N 2005/0646; A61N 2005/0647; A61N 2005/0648; A61N 2005/0649; A61N 2005/0667
  See application file for complete search history.

(56) References Cited

U.S. PATENT DOCUMENTS

| | | | |
|---|---|---|---|
| 2001/0010019 A1* | 7/2001 | Schachar | A61F 2/14 623/4.1 |
| 2005/0113806 A1* | 5/2005 | De Carvalho | A61F 2/02 604/890.1 |
| 2006/0271025 A1* | 11/2006 | Jones | A61F 9/00802 606/4 |
| 2010/0241100 A1 | 9/2010 | Blumenfeld et al. | |
| 2010/0249691 A1* | 9/2010 | Van Der Mooren | A61F 9/00781 604/9 |
| 2012/0209051 A1 | 8/2012 | Blumenkranz et al. | |

FOREIGN PATENT DOCUMENTS

| | | | |
|---|---|---|---|
| CN | 102573813 | 7/2012 | |
| JP | 2002522111 A | 7/2002 | |
| JP | 2011212115 A | 10/2011 | |
| WO | 200007515 A1 | 2/2000 | |
| WO | 2001/028473 | 4/2001 | |
| WO | 2002/074196 | 9/2002 | |
| WO | 2003/009784 | 2/2003 | |
| WO | 2006/058189 | 6/2006 | |
| WO | 2008/011125 | 1/2008 | |
| WO | 2012/058382 | 5/2012 | |
| WO | WO 2013024437 A1 * | 2/2013 | ........ A61N 1/0526 |

OTHER PUBLICATIONS

Written Opinion for Singapore Application No. 11201502274X, dated Jun. 21, 2016 (7 pages).
First Office Action and English Translation of First Office Action for Chinese Application No. 2013800526504, dated May 16, 2016 (15 pages).
International Search Report, PCT/EP2013/070918, dated Oct. 13, 2013.
Office Action and English translation thereof for Japanese Patent Application No. 2015-535059, dated Jul. 25, 2017 (6 pages).

* cited by examiner

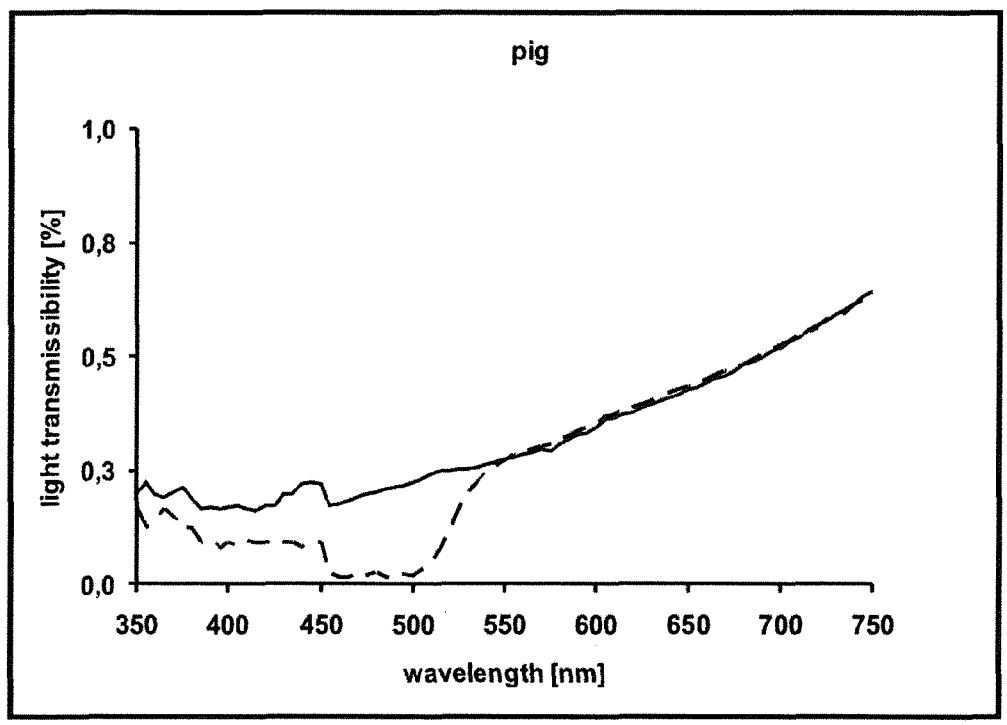
Fig. 8e
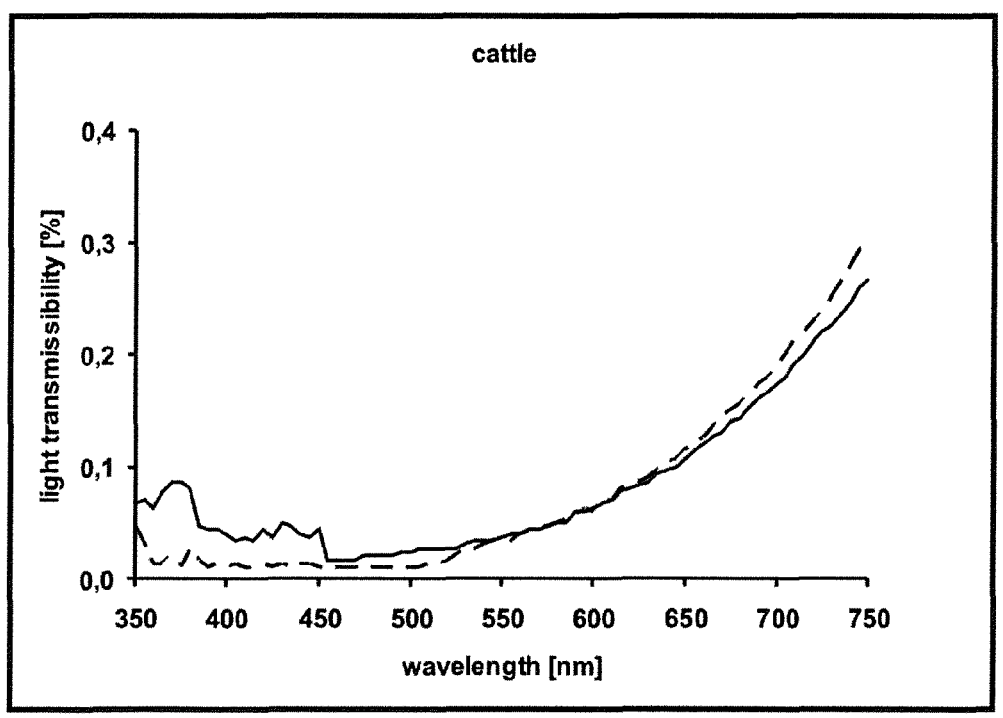
Fig. 8f
Fig. 8

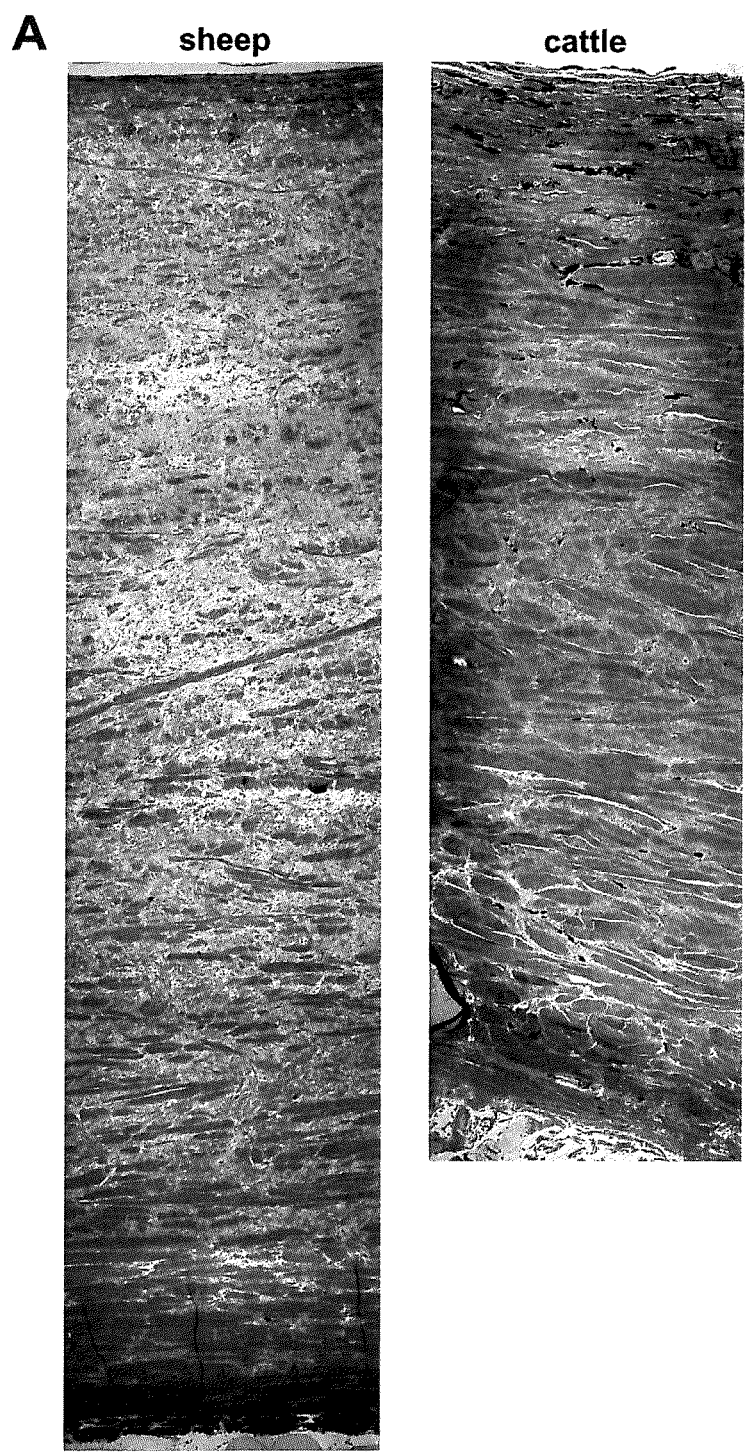
Fig. 10 A (to be continued)

Continuation of Fig. 10 A

DEVICE FOR A MEDICAL TREATMENT OF A SCLERA

This application claims benefit from International Application No. PCT/EP2013/070918, which was filed on Oct. 8, 2013, which claims priority to European Patent Application No. EP 12187675.9, which was filed on Oct. 8, 2012, the entireties of said patent applications are incorporated herein by reference.

FIELD OF THE INVENTION

The present invention generally relates to a substance application and radiation system (SARS) (also called "substance application and irradiation system" (SAIS)) for the treatment of the sclera-tissue of the eye. Thus, the invention relates to a medical device for substance application (and/or radiation) during ophthalmological surgical procedures on a patient. In particular, the invention relates to a device for medical treatment of a sclera.

BACKGROUND OF THE INVENTION

Collagen cross linking (by applying riboflavin and UV-A light radiation) has been used in the past years in ophthalmology for the treatment of patients with maceration diseases of the cornea (the translucent part of the adventitia in the front part of the eye) (Wollensak et al., American Journal of Ophthalmology 2003, 135:620-627). The application of substances and light is significantly easier in the front part of the eye, since this part can be reached directly without surgical procedures.

Collagen cross linking of the sclera for the treatment of progressive myopia (scleral cross linking) is new and has so far only been tested in animal experiments (Iseli et al., Journal of Refractive Surgery 2008, 24:752-755; Wollensak et al., Acta Ophthalmologica Scandinavica 2005, 83: 477-482).

At this point in time there is no system for substance application or radiation for an extensive treatment of the outer part of the eye (especially the posterior and equatorial areas of the sclera) for the treatment of pathological deformation of the sclera. On the one hand, this therapeutic approach for the treatment of progressive myopia (scleral cross linking through riboflavin and blue-light therapy) is completely new, and on the other hand, there are no therapeutic approaches for other diseases that would have required a large-scale substance application-/radiation system in ophthalmology.

In the inventor's experimental research, the photosensitive substance (riboflavin) was dripped into the Tenon's space and radiation ensued with a light application system (Bluephase 16i, Ivoclar Vivadent GmbH, Ellwangen-Jagst, Germany) which was designed for use in dentistry. For the use in our field, the inventors made several modifications (such as certain attachments to regulate the amount of light-energy). An extensive and homogenous radiation especially of the rear areas of the sclera is not possible with this auxiliary system. Substances have to be applied separately and alternating with radiation and will spread unevenly throughout the entire Tenon's space. This system is completely unsuitable for use in human eye surgery, since, inter alia, it cannot factor in the anatomy (size and shape of the human eye, muscle and nerve endings, vascular anatomy, etc).

Known instruments for substance application are designed for the localized application on the fibrous connective tissue directly on the sclera (episclera, sub-Tenon's space). Known patents describe a substance application under the episclera/sub-Tenon's space (WO 01/28473 A1, US 2010/0114039 A, WO 03/009784 A1) or they are meant for the localized application on the conjunctiva (WO 2010/105130 A2). These applications are aimed at small-scale, rather selective treatment of the retina; i.e. the sub-scleral tissue in the innermost part of the eye (see also FIG. 1). The substance thus has to first penetrate the outer tissue of the eye such as sclera and choroidea to reach its target location, the retina. The known systems only use the exterior application to the sclera to avoid the surgical application directly into the eye on the surface of the retina. These methods still bear the risk of post-surgical inflammation and injuries of the adventitia of the eye and are also not designed for the treatment of scleral tissue. The therapeutic aim of these treatment methods is thus a completely different one. The substance application and radiation system (SARS) according to the present invention is applied directly to the site of the sclera that is to be treated in the Tenon's space (the space between the eye and the orbital cavity) (see FIG. 6). The presently claimed system is positioned exactly where the treatment site is; i.e. the outer scleral tissue. Our approach does not involve any increased risk of complications during and after surgery vis-à-vis established surgical methods.

Applicators that have been described so far are used to form or release depots for medicine (WO 01/28473 A1, US 2010/0114039 A) and are not designed to release medicine/agents during surgical treatment and to then be removed again after surgery.

WO 03/009784 A1 suggests to implant a medication depot permanently into the sub-Tenon's space, it will thus not be removed at the end of surgery. As has already been mentioned, all of these applicators have the retina as primary target tissue. The present application is directed to the treatment of the sclera. None of the applicators is capable of covering the sclera sufficiently for treatment. All existing applicators have to be understood as local small-scale applicators, they affect a completely different target tissue and have different treatment approaches for different diseases. Additionally, all applicators cannot really regulate the substances application/delivery. Furthermore, none of these applicators can ensure an undesired diffusion of the substances and that adjacent tissues will not be affected by the treatment.

WO 2012/058 382 A2 describes a device for delivering an active agent to target tissue at a site that includes a bodily fluid. The device includes a body having a first exterior surface including a first section having a local, discrete recessed area formed in the body for holding the active agent. The body includes a surface flow feature in the form of a canal that is formed in the body and is recessed relative to the exterior surface. The surface flow feature interfaces with the first section and the local recessed area and is configured so as to guide or modify flow of the bodily fluid relative to the body such that fluid communication is provided between the bodily fluid and the local recessed area. The local recessed area is recessed relative to at least a portion of the canal. The device can also be in the form of a device that has an erodible member that releases the active agent over a prescribed period of time.

WO 2006/058 189 A2 provides a medical device having a thermister for temperature measurement, irrigation/aspiration ports for fluid exchange and application of therapeutic modalities, a pressure manometer for pressure measurement, and an external system for control of temperature, pressure, and flow rate. When applied to the eye and orbit, this device can be used in hypothermia or hyperthermia applications, the control of intraocular pressure (IOP), and the application of treatment modalities. Methods of using the device in treating patients suffering from central retinal artery occlusion, anterior optic nerve disease, pathology of the choroid and retina including the macula, inflammation of the eye including the vitreous and anterior segment, glaucoma, inflammation and/or infections of the anterior and/or posterior segment of the eye, treatment before/during/after surgery of the eye, and the application of treatment modalities through a semipermeable membrane are described.

In WO 2008/011 125 A2, devices, systems and techniques for delivering drugs to an ocular tissue are described. In at least some embodiments, a terminal component (e.g., a needle or open end of a catheter) is implanted in an ocular tissue and used to deliver one or more drugs. The delivered drugs may come from a source which is also implanted, or may be introduced from an external source (e.g., via a port). Both solid and liquid drug formulations can be used. Ocular implants can alternatively include a thin film coating that releases a drug into an ocular tissue.

U.S. Pat. No. 5,725,493 A discloses an intravitreal medicine delivery device and method including an implant device through which a wide variety of beneficial medicines including drugs or other pharmacological agents can be introduced into the vitreous cavity over an extended period of time with only a single initial surgery to implant the device. The device and method minimize the surgical incision needed for implantation and avoid future or repeated invasive surgery or procedures. Additional amounts of the initial medicine can readily be introduced or the medication can be varied or changed, as required. Furthermore, the device and method allow the dosage delivered to the vitreous cavity to be controlled, and the device is constructed so as to filter medicines delivered to the cavity and also avoids damage to or interference with other parts of the eye during implantation or during use.

WO 02/074 196 A1 describes ocular implant devices for the delivery of a therapeutic agent to an eye in a controlled and sustained manner. Dual mode and single mode drug delivery devices are illustrated and described. Implants suitable for subconjunctival placement are described. Implants suitable for intravitreal placement also are described. The invention also includes fabrication and implementation techniques associated with the unique ocular implant devices that are presented herein.

None of the existing prior art describes the introduction of separate systems into the same application system (e.g. agent/substance and electromagnetic waves, or the application of different separate agents) which can be essential for the method of collagen cross linking. None of the prior art allows for the control of a finely tuned localized medication release or a simultaneous dosing of the radiation. Suction systems for superfluous substances/agents are also not provided for in these applicators.

So far, there is no application system which is suitable for use on the sclera with the new treatment approach according to the invention. Existing substance applicators are designed for localized application of substances in cases when the tissue targeted for treatment is not the sclera but the underlying tissue (mostly the retina in the inner part of the eye). The presently claimed applicator can apply substances extensively and in a controlled manner to all parts of the sclera, which has not been possible so far.

A shortcoming in the system that has so far been used in animal experiments is the size of the radiation unit in restricted spaces, which leads to severe or dangerous manipulation of the eye. An extensive and homogenous radiation also of the back parts of the sclera is not possible with this auxiliary system. Furthermore, the radiation system only radiates in certain predetermined time intervals. It is not possible to freely control the radiation energy levels. Since the only light power settings in the radiator employed by us were 50% or 100%, auxiliary plastic attachments had to be developed which enabled the use of graduated light power levels. Substances could only be applied by dripping them onto the tissue which leads to an inhomogeneous distribution of the substance. Thus, the substance also reaches tissue areas that are not supposed to be treated. Moreover, substance applicators and parallel systems (e.g. light) cannot be used simultaneously. There are no specially formed suction systems. So far, it is also not possible to extensively treat the middle and rear part of the eye/sclera.

The invention resolves disadvantages of the auxiliary system from the animal experiments and of other systems and treatment approaches respectively. Such disadvantages are:
  anatomically unsuitable for extensive/comprehensive treatment of the sclera in view of the anatomy of the treated eye
  so far, only small-area, isolated and serial treatment/substance application is possible (e.g. by specially formed needles—WO 01/28473), the treatment of large areas of the sclera can thus not be performed or only with long hours of surgery (WO 01/28473, US 2010/114039)
  the locally or temporally parallel application of different substances is not possible
  a temporal and local combination of substance application and electromagnetic radiation (e.g. light) is not possible; the necessary alternation between the application of substances and light leads to a considerable increase in the duration of surgery/treatment
  since substance and light applicators have to be attached and detached periodically alternating, the treatment becomes inhomogeneous because the surgeon has to constantly rearrange everything; moreover, the attaching and detaching bears an increased risk of damaging the surrounding tissue
  lighting elements that are known thus far do not produce an homogeneous lighting of the tissue to be treated
  there is no return/suction system for superfluous substances, tissue not to be treated is always affected/co-treated
  there is no protection for radiation sensitive substances from the radiation until the radiation has arrived at the application-/treatment site (no shielding of the substance feeding exists)
  known application systems cannot be introduced under visual control (video system)

So far, there is no application system that is suitable for use on the sclera or the treatment approach according to the invention. The therapeutic approach for the treatment of progressive myopia or pathological changes due to sclera maceration is completely new. Therefore, there is no surgical equipment that meets the requirements of this method of treatment or this surgical procedure. Individual technical methods for substance application or for the radiation of areas/tissue are always streamlined for their specific uses and do not fulfil the requirements of our therapeutic approach. There is a need for an extensive system for the homogeneous substance application and/or radiation that takes the exact anatomic structure of the eye into account and meets all the technical requirements of the treatment or the surgical procedure.

The disadvantages and shortcomings of the substance application and the radiation unit used in the animal experiments would also be eliminated by the new application system (SARS).

SUMMARY OF THE INVENTION

Accordingly, one aspect of the invention relates to a device for a medical treatment of a sclera, the device comprising a curved disc, wherein: the disc is configured to be placed into the Tenon's space; the disc is formed such that the inner surface of the curved disc is superficially contactable to the surface of an area of the sclera so as to superficially cover said area; and the disc comprises one, two, three, four, or more independent channel systems.

Here and in the following, the inner surface of the disc is defined as the concavely curved surface of the disc, and the outer surface of the disc is defined as the convexly curved surface of the disc.

The disc may have the form of an elongate bowl, for example an ellipsoidal cap or a spherical cap, having preferably a length between 10 mm and 30 mm, more preferably a length between 15 mm and 25 mm, or most preferably a length of 20 mm, and having preferably a width between 5 mm and 25 mm, more preferably between 8 mm and 20 mm, or most preferably between 10 mm and 15 mm, and wherein the thickness of the disc is lower than or equal to 5 mm, or preferably lower than or equal to 3 mm, and has preferably a minimum of 2 mm.

Here, the length can be defined by the length of a first straight line segment virtually connecting two points on the edge of the disc having maximal distance; and the width can be defined by the length of a second line segment, wherein the second line segment is the longest line segment being perpendicular to the first line segment and virtually connecting two points on the edge of the disc.

In one embodiment of the device according to the invention, one or more recesses are formed in the edge of the disc. Preferably, the one or more recesses are positioned and formed such that the recesses leave free space for eye muscles, blood vessels and/or nerves when the disc is positioned on said area of the sclera.

In a further embodiment of the invention, the disc comprises a base layer made from a material preferably being sterilisable and/or heat-resistant, for example medical steel.

Further, the disc can comprise one or more additional layers, wherein the base layer and the one or more additional layers are arranged as stacked layers with the base layer on the outer side of the disc so as to support the additional layers. Each of the one or more additional layers can be made from a plastic or a metal material. Each of the one or more additional layers can also be made from a light-diffusing, light blocking and/or sponge like material.

The disc or at least one of the layers forming the disc may alternatively be made from another suitable material such as a polymer. In particular, the disc or at least one of the layers forming the disc may be made by a flexible material.

The disc or one of the layers forming the disc may be made of a material suitable for being used in a 3D printer. The disc may then be produced by printing it monolithically as one piece. Alternatively, the disc may be formed of several printed layers that can be plunged, stuck, and/or adhered together in a suitable way. Also, the disc or one of the layers forming the disc may be produced by a cireperdue process or the like. Further, the inner surface and/or the outer surface may be metallised or coated. Also, the (inner) surface of the channels may be coated using a liquid.

In a preferred embodiment of the device, each of the channel systems comprises a first channel having a proximal end on the edge of the disc or extending beyond the edge of the disc, wherein the first channel at the distal end either splits into two or more second channels or has a distal opening, wherein each of the second channels at the distal end again either can split into two or more third channels or has a distal opening, and wherein the splitting of the channels can be further repeated such that each of the channels either splits into two or more channels or has a distal opening.

Here, the number of subsequent splits within a channel system may be limited to one, two, three, four, five, or six.

A channel system as described above is a tree-like formed delivery system, wherein the first channel can be considered as the central "trunk" and the second, third, or higher-ordered channels can be considered as twigs or branches. Here, the term "distal" shall define at any point within the channel system a direction according the direction of flow, when the flow (of agent, liquid, electromagnetic radiation, etc.) is conducted from the side of the trunk opposite to the twigs into the twigs. A "distal end" then refers to a spot in the channel system, where the flow leaves a channel. This definition of "distal" shall also hold, when the actual direction of flow is reversed (for example, for a suction system as disclosed below, wherein the upstream direction corresponds to the distal direction). Further, at any point, the term "proximal" shall refer to the direction opposite to the "distal" direction. Accordingly, the expression "proximal end" refers to the end of the trunk on the opposite side of the twigs.

In one embodiment, at least part of the distal openings being arranged on a surface of a layer are formed as elongate openings, wherein, for example, an elongate opening may be formed such that part of the channel having the elongate opening is shaped as a half-cylinder with its round side being embedded in the respective layer and being open in the direction pointing away from the respective layer.

The distal openings of at least a part of the channel systems may be regularly distributed with respect to the plane of the disc. The plane of the disc can be virtually subdivided into different areas having different distributions of the openings.

Alternatively, the distal openings of at least a part of the channel systems may be irregularly or randomly distributed with respect to the plane of the disc.

Also, the density of the distal openings of at least a part of the channel systems may be variable with respect to the plane of the disc.

In one embodiment of the device, the disc has a symmetric shape. The distal openings of at least a part of the channel systems may be arranged symmetrically in accordance with the symmetry of the disc.

In a further embodiment of the invention, the channels systems are embedded in the base layer. Each of the openings at a distal end of a channel can be arranged on the inner surface of the base layer. Also, the channel systems may be at least partly embedded in the base layer. Further, the channel systems may be at least partly embedded in one or more of the additional layers, wherein each of the openings at a distal end of a channel is arranged on the inner surface of the base layer or within one of the additional layers or on the surface of one of the additional layers.

In one embodiment, at least part of the channel systems are configured as agent channel systems such that the channels of each of the agent channel systems are tubes adapted to lead an agent.

The channels of at least part of the agent channel systems may be at least partly isolated against electromagnetic radiation. For example, they may be isolated against electromagnetic radiation with a wavelength in the range between 100 nm and 2000 nm, and most preferably isolated against electromagnetic radiation with a wavelength in the range between 300 nm and 800 nm.

In one embodiment of the invention, the inner surface of the disc has a structure adapted to allow for an improved distribution of agent when agent is lead through the agent channel system(s), and wherein the surface structure preferably comprises chamfers, or elements such as bars, half-spheres, pyramids or cones.

In one embodiment, at least one of the additional layers is made from a sponge or a sponge-like material or a porous material preferably being sterilisable and/or heat-resistant, and wherein at least part of the distal openings of at least part of the agent channel systems are arranged within or at the outer side of the layer(s) made from a sponge or a sponge-like material or a porous material.

In a further embodiment of the device, the proximal end of the first channel of each of the agent channel systems is connectable to a separate agent supply.

In a preferred embodiment of the device, at least part of the channel systems are configured as optical guiding systems, wherein each of the optical guiding systems is adapted to guide electromagnetic waves from the proximal end of the first channel to the distal openings of the optical guiding system.

In one embodiment, the channels of the optical guiding system(s) comprise one or more bundles of optical conductors, for example optical fibres, wherein at each split of a channel, the bundle comprised in the channel is fanned out into a number of smaller bundles, the number of smaller bundles corresponding to the number of the two or more subsequent channels, such that each of the two or more subsequent channels comprises one of the smaller bundles.

In one embodiment, at least one of the additional layers is a diffuser adapted for diffusing electromagnetic waves, and at least part of the distal openings of at least part of the optical guiding systems are arranged within or at the outer side of the additional layer(s) being a diffuser.

The diffuser(s) can be made from a material being sterilisable and/or heat-resistant and/or biocompatible. The diffuser(s) can, for example, be made from suitable polymers or plastic.

In one embodiment of the invention, the device comprises two, three, four, or more independent optical guiding systems. The two, three, four, or more independent optical guiding systems may cover separate areas. Preferably, each of the optical guiding subsystems is adapted for guiding a certain range of electromagnetic radiation In a further embodiment of the device, the proximal end of the first channel of each of the optical guiding systems is connectable to a source of electromagnetic radiation.

In a preferred embodiment, each of the independent optical guiding systems can be supplied independently with electromagnetic radiation.

In one embodiment of the device, at least one of the channel systems is configured as a cleaning system such that the channels of the cleaning system(s) are tubes adapted to lead an agent. Preferably, the distal openings of each of the cleaning system(s) are arranged on the outer surface of the disc and/or on the edge of the disc.

In a preferred embodiment of the invention, at least one of the cleaning system(s) is configured as a suction system, wherein the proximal end of the first channel of each of the suction system(s) is connectable to a pump means. At least one cleaning system may be configured as a flushing system configured to deliver one or more agents to the distal openings, wherein the suction system(s) and the flushing system(s) are identical cleaning system(s) adapted for suction and flushing in an alternative manner, or wherein at least one cleaning system is configured as suction system and at least one further cleaning system is configured as flushing system.

The suction system(s) may be constructed such that its distal openings are covered by a strainer, filter, mesh, or a porous material suitable for preventing tissue from being sucked by the suction system(s) and/or for avoiding that the suction system(s) become clogged.

In a further embodiment of the device, a handle is arranged at the edge of the disc. The handle can be arranged as a tube, and the first channel of each of the channel systems may extend through the handle.

In an alternative embodiment, the handle is connectable with the edge of the disc. The handle can be arranged as a tube, and the first channel of each of the channel systems can be conducted through the handle.

Preferably, the outer surface of the disc and/or the edge of the disc is impervious to light. The channel system may also be impervious to light.

In one embodiment, the outer surface of the disc and/or the edge of the disc is impervious to electromagnetic radiation. For example, the outer surface of the disc and/or the edge of the disc is impervious against electromagnetic radiation with a wavelength in the range between 100 nm and 2000 nm. As another example, the outer surface of the disc and/or the edge of the disc is impervious against electromagnetic radiation with a wavelength in the range between 300 nm and 800 nm.

In yet an embodiment, the device further comprises one or more sensor(s) or measurement system(s). The one or more sensor(s) or measurement system(s) can comprise a temperature sensor and/or a camera system and/or biomechanical sensor, preferably a pressure sensor, and/or a pH meter. Also, the device may further comprise a cooling system.

The device according to the invention:
can be adapted to anatomy and size of the eye
enables extensive treatment of the scleral tissue (also of the posterior sclera)
enables temporally and locally controlled use of different systems (e.g. substance application and suction, radiation, visual control)
a homogeneous, extensive distribution of substances is possible due to surface modifications on the inside and outside of the system (impossible when using cannulas).

The substance application and radiation system enables the extensive treatment of the outer sclera (the white tissue of the eye) for scleral collagen cross linking. Through the application of special chemical substances and/or light of different wavelengths to the sclera it is possible to cross link collagen molecules and thus change the biomechanical properties of the tissue. Thus, certain pathological changes and diseases of the eye (e.g. progressive myopia, scleritis, tissue-macerating inflammation) could be treated. These pathological changes minimize the biomechanical stability of the sclera and lead to an abnormal expansion of the eyeball and consequently to serious visual limitations or blindness.

Furthermore, the substance application and radiation system (SARS) according to the invention enables the extensive treatment of the outer sclera (the white tissue of the eye) for scleral cross linking for the treatment of progressive myopia, pathological changes of the sclera or other biomechanical maceration symptoms that can be brought about by different causes (e.g. inflammation, local infections, scleritis). The therapeutic approach to these special diseases of the eye is new and requires—due to the complex anatomy of the eye—a surgical application system with adapted shapes and certain technical features.

BRIEF DESCRIPTION OF THE DRAWINGS

The invention will now be described in detail with regard to the following drawings.

DETAILED DESCRIPTION OF EMBODIMENTS

Protein (e.g. collagen) cross linking is a method established in biotechnology. The cross linking of proteins can be effected by chemical cross linkers/agents or through photosensitive substances with subsequent radiation (e.g. riboflavin application and UV-A-light or blue light radiation).

Collagen cross linking is thus supposed to induce a connection of the molecules which change the biomechanical properties (stiffening). Collagen cross linking through riboflavin application and UV-A-light radiation has been used for some years in ophthalmology for the treatment of patients with maceration diseases of the cornea (translucent part of the adventitia in the front part of the eye) (Wollensak et al., American Journal of Ophthalmology 2003, 135:620-627). Substance and light application are much easier in the front part of the eye since this part can be reached directly without surgery. However, the problems of the inhomogeneous radiation and substance distribution have not been completely eliminated here either.

Collagen cross linking of the sclera (scleral cross linking) for the treatment of progressive myopia and other maceration diseases is new and has so far only been tested in animal experiments (Iseli et al., Journal of Refractive Surgery 2008, 24:752-755; Wollensak et al., Acta Ophthalmologica Scandinavica 2005, 83: 477-482). All technical means in the animal experiments have various disadvantages and are not suitable for the use with patients.

Additionally, proteins and collagen can be crosslinked by an application of solely crosslinking chemical substances without a subsequent radiation (see "Chemical crosslinking and the stabilization of proteins and enzymes" by Wong S S, Wong L J. Enzyme Microb Technol. 1992 November; 14(11):866-74).

With the device according to the invention it is possible for the first time to extensively supply the rear and equatorial parts of the sclera with agents from the outside. Simultaneously, other systems can be used. Superfluous agents are removed. Additional modifications of the surfaces allow a better distribution of agents, and a better removal of the agents in the areas not to be treated, respectively. The device according to the invention is the prerequisite for a time saving (short surgery times) application of a new therapeutic approach with patients and in animal experiments. The device according to the invention is ergonomically adapted to the anatomy of the human eye. Its materials are sterilizable and reusable.

The present invention allows for the locally and temporally controlled release and back flow of agents (e.g. substances, medicines) and allows the combination with other physical applications (electromagnetic radiation) on defined areas of the sclera. The present invention additionally allows for the locally and temporally controlled irradiation and application of defined power levels of electromagnetic radiation (i.e. energy amount per time and area)

Figure 1:
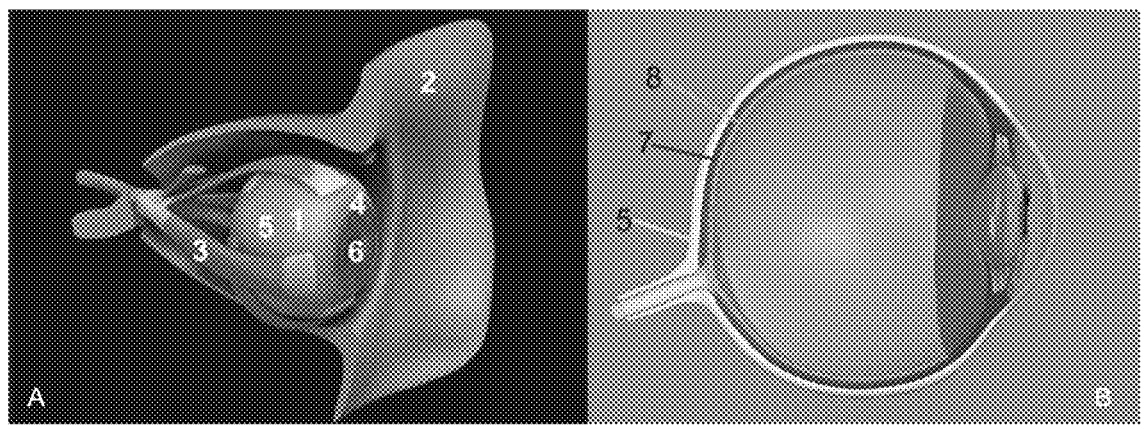
FIGS. 1A and 1B show detailed representations of the eye's anatomy and its adnexa.

The outer, surrounding collagenous layer of the eye is the sclera (white part) and the cornea (translucent part; FIG. 1). In some diseases, this tissue part of the eye is weakened. This can be the case with respect to biomechanical stability, enzymatic resistance to digestion or in respect to its swelling behaviour. This debilitation of the eye (cornea and sclera) can be positively influenced through cross linking. For this, an agent (fluid) has to be introduced into the respective tissue layer of the eye, either with or without additional additives e.g. electromagnetic radiation, a second agent), to start chemical or physical reactions. These reactions lead to changed biomechanical properties and to an improvement of the treated layers of the eye with respect to the above-mentioned weaknesses. This treatment is called "cross linking".

FIGS. 1A and 1B show detailed representations of the eye's anatomy and its adnexa. The left image (FIG. 1A) shows the eye 1 in the orbital cavity (bone 2) with its muscular connections 3. The eye 1 lies in the orbital cavity in a periscleral lymph space, the Tenon's space which is usually closed to the front between the corneal limbus 4 and the eyelid (not shown here). The sclera 5 is the white part of the outer eye, the cornea 6 the translucent part of the eye 1.

Both tissues are made from collagenous tissue. The right image (FIG. 1B) shows a detailed labeling of the anatomical layering of the inner tissues of the eye 1. In the right image, the tissue structures of sclera 5/choroid 7/retina 8 are highlighted.

In the scleral part, the eye ball is surrounded by a very thin submucosa, the episclera (not shown separately), which is connected to the sclera 5.

The device according to the invention enables the extensive treatment of the outer sclera for scleral collagen cross linking. The device (SARS) according to one embodiment preferably is a flat, large-scale and spoon-like bent ophthalmological surgical instrument with variable areal shape for the dosed release of substances/agents to the sclera or parts of it (see FIG. 2). In the shown embodiment, the device consists of a carrier plate (outer part of the SARS) and an inner part, the diffuser. The areal shapes, i.e., the exact dimensions and measurements of the SARS can be varied. The approximate dimension of the very simple areal shape (FIG. 2A) is about 10 to 15 mm in width and about 20 mm in length (since the SARS is adapted to the concavity of the eye, it is preferably 30 mm). The thickness of the whole SARS should preferably not exceed 3 mm.

FIGS. 2A-2F show schematic representations of the approximate dimensions and possible areal shapes of the device of the invention according to a preferred embodiment. FIG. 2A, shows a view of the interior of the device 100 and the approximate measurements. FIGS. 2B and 2C show the dimensions from a lateral view and the positioning of the carrier plate 102 and the diffuser 103. FIG. 2D shows a rather simple and 2E shows a modified version of the applicator having recesses 10 and 12. FIG. 2F shows shapes that are adapted to the shape of the eye and the sclera of a human eye in the nasal (towards the nose) and temporal (towards the side) directions and which take the anatomically distinctive features of muscles and vessels into account.

Figure 2:
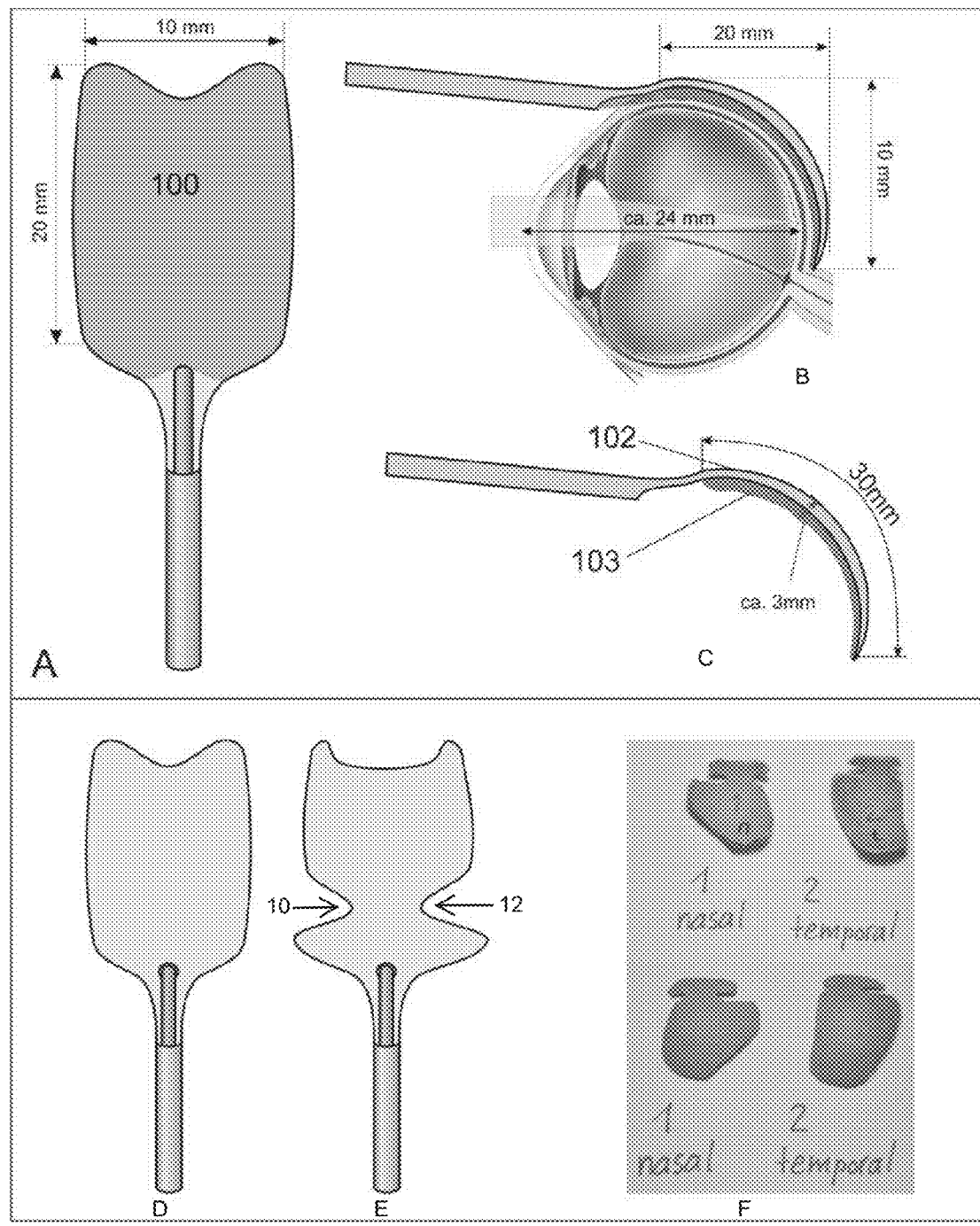
FIGS. 2A-2F show schematic representations of the approximate dimensions and possible areal shapes of the SARS.

The exact areal shapes and dimensions of the SARS result from the precise anatomical characteristics of the eye or even of the individual patient or the individual patients clinical and therapeutical needs. Furthermore, the exact areal shapes and dimensions of the SARS result from the determined minimal areas that need to be treated for growth inhibition. Therefore, the SARS can have varied shapes, preferably areal shapes, that are of simple or complex form or that may even be calotte-shaped and cover the whole scleral part of the eye (FIG. 2).

Figure 3:
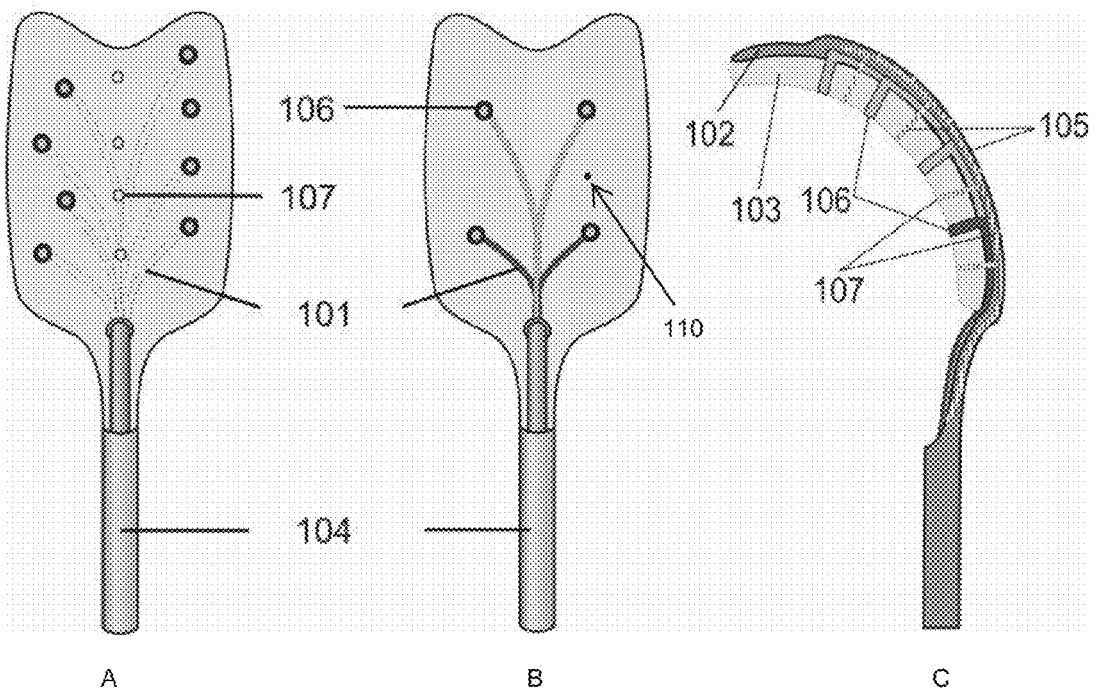
FIGS. 3A-3C show schematic representations of possible arrangements of afferent and efferent channels of the SARS.
Figure 4:
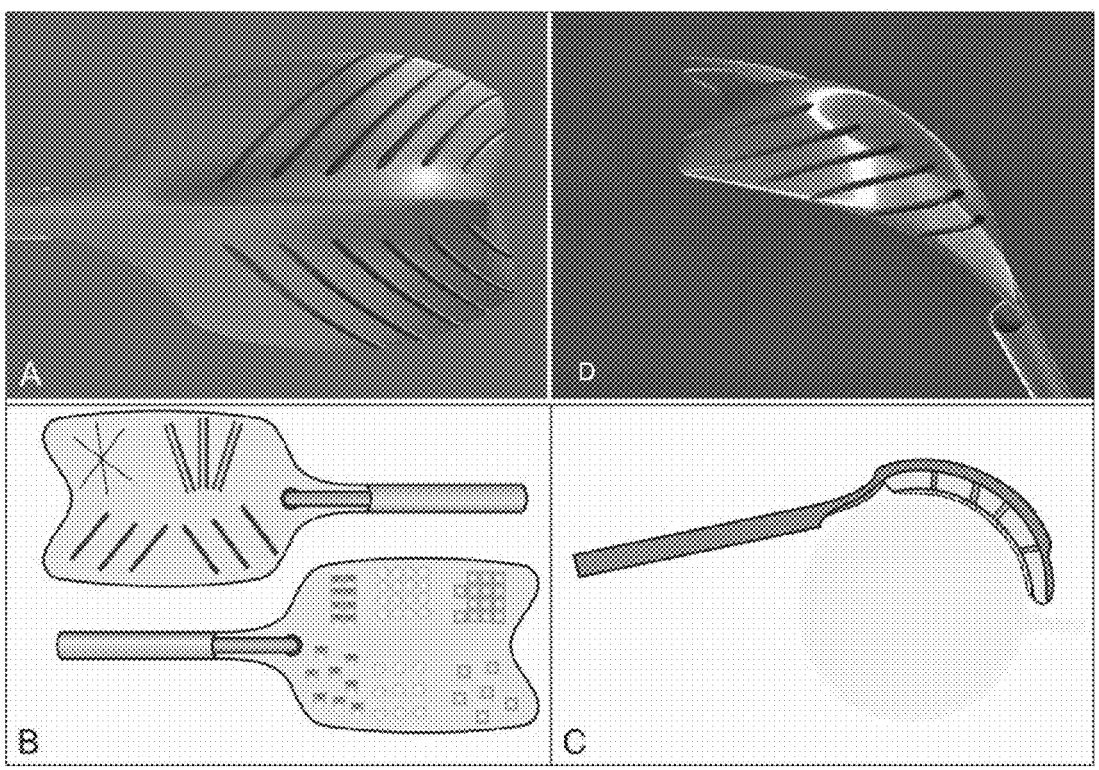
FIGS. 4A-4D show schematic representations of possible surface modifications of the SARS.
Figure 5:
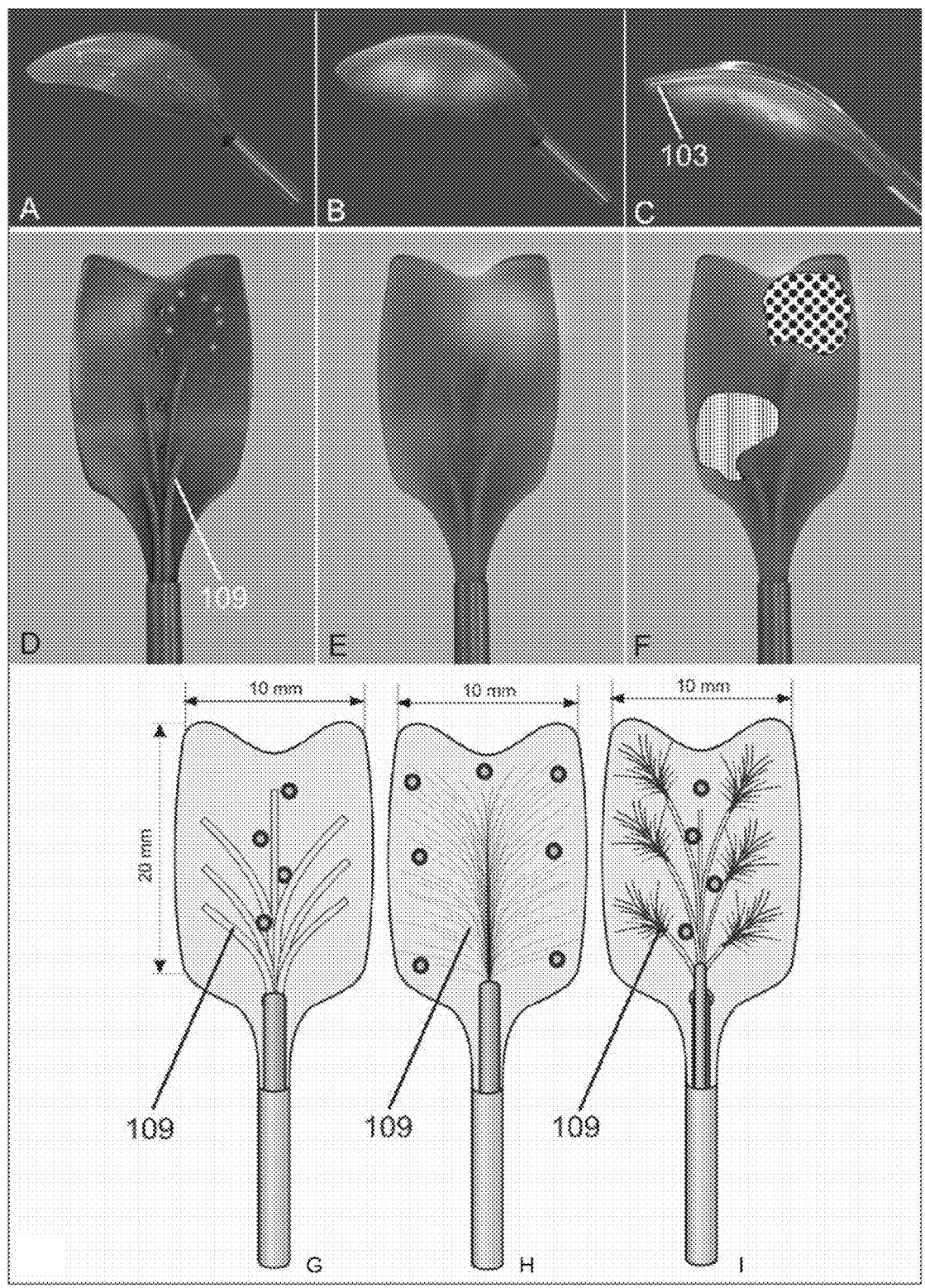
FIGS. 5A-5I show schematic representations of possible arrangements of the optical fibers within the diffuser of the SARS.

FIGS. 3 to 5 only exemplarily show the simple areal shape, to provide a clear representation and an easy to understand explanation of the respective facts. All further modifications of the device can of course be applied to all other areal shapes as well.

The homogeneous substance distribution is realized by a defined arrangement of afferent channels 101 in the carrier plate 102 and is supported by defined surface modifications of the inside of the device 100. The afferent channels 101 can be controlled in groups or separately since they are connected to an external multi-pumping system via the shaft 104. It is thus possible to control the substance application temporally and locally. The number of channels per area can vary.

The suction is also performed with a specially arranged system of channels 105 which has openings 107 on the inside (towards the eye) as well as on the outside. All channels of this system can be regulated by a controllable negative pressure suction system. In this case, it would not be necessary to be able to control single channels separately. However, it would be possible to technically realize such separate control.

The system of channels 101, 105 for the feeding and removal of substances/agents is integrated into the carrier plate 102, which is made from solid material (e.g. surgical steel) and has to be able to withstand several forms of disinfection.

FIGS. 3A-3C show schematic representations of possible arrangements of afferent 101 and efferent 105 channels of the SARS. FIG. 3A shows possible arrangements of the channels on the inside of the device (looking on the inside of the SARS). The arrangement of the channels can be symmetrical, offset, or arbitrary or have other patterns. FIG. 3B shows the inside of the carrier plate 102 with afferent channels 101 and their openings 106 towards the inside. The grey shades different colours symbolize the simultaneous application of two different substances. Additionally, sensor or measurement system 110 is schematically shown in FIG. 3B. FIG. 3C shows the system of channels of the device from the side. Light and dark grey coloured afferent channels symbolize two different substances of a simultaneous application. The afferent system of channels 101 has channels openings 106 through the inner part of the device, the optical diffuser 103, on the side facing the eye. The suction system (black and white striped) has channels openings 107 on the inside and on the outside of the SARS. The afferent and efferent channels systems are mainly integrated into the carrier plate 102, but they also penetrate the diffuser (inner part of the device) with small channels.

The device according to the invention can be modified with different surface shapes and materials on the inside and/or the outside to ensure a homogeneous substance distribution during agent application and an unhindered removal of the substances in the efferent system (FIG. 3). Thus, different surface structures (e.g. hemispheres, pyramids, cones, bars, grooves or the like) can be introduced in/applied to the inside (diffuser part) and/or the outside (carrier platform). The arrangement can be variable and can be organized in different patterns (e.g. symmetrically or arbitrarily). Specific groove or channels patterns can also be introduced in/applied to the inside (diffuser part) and/or outside (carrier platform). Different materials with diverging porous structures (e.g. sponge-like) can also be placed on the inside.

FIGS. 4A-4D show schematic representations of possible surface modifications of the SARS. FIGS. 4A and 4D show a possible arrangement and a possible orientation of integrated channels on the outside of the device (looking on the outside of the carrier platform of the SARS). The channels lead to a central efferent channel in the back of the carrier platform. FIGS. 4B and 4C show possible surface geometries (bars, channels, star-shaped arrangement, hemispheres, pyramids, cones) with diverse orientations and arrangements (as complete inner surface, as aggregates, or individually in variable arrangements). FIG. 4C illustrates the SARS placed onto the eye, with a sponge-like surface material (black-white striped) on the inside of the SARS.

In addition to the substance application, the device can be combined with a radiation system that enables an extensive radiation of the scleral tissue. Irradiation is realized by optical fibers 109 that can be directed to the inside of the SARS through the shaft and that can then be distributed in the diffuser 103 (inner part of the device) in various ways, depending on the chosen arrangement (see FIG. 5). The optical fibers 109 can extend both in the diffuser and in the carrier plate until they exit (light emission at the end of the optical fibers 109). Alternatively, the optical fibers may end at the transition zone between the shaft and the applicator disc(s).

The inner part of the device is designed by the diffuser 103. The diffuser 103 is to provide for a homogeneous extensive illumination so that no "hot spots" with a high amount of radiation energy or areas with too little light energy levels occur. This is made possible by the material properties of the diffuser. The diffuser is made from a material (e.g. various artificial polymers) that is heat resistant, that can be disinfected in an accepted manner and that is biocompatible. The optical properties of the diffuser material contribute to the extreme diffusion of the radiation from the ends of the optical fibers. Here, different diffuser material with certain diffraction and diffusion properties can be used in the construction of special device with certain wavelength preferences/limitations. When the diffuser's polymer itself does not have diffusive properties, it is possible to combine the polymer with optically diffusing elements (e.g. polymer-beads in different shapes and sizes) during manufacturing. Another alternative is to modify the surface of the diffuser material in order to reach the desired optical diffusive effects (e.g. roughening of the surface).

The optical fibers (also called optical waveguide or glass fiber) can be selected in different realizations and have to be able to conduct electromagnetic radiation of different wavelengths (UV light to infra red light, from approximately 30 nm-1100 nm). Some structural realizations of the SARS can then be optimized for specific wavelengths of the electromagnetic radiation and specific light energy levels. Thus, specific optical fiber materials (e.g. extra UV light conductive) and specific optical fiber diameters (e.g. larger cable diameters for high energy levels) can be used for the SARS. The optical fibers of the device should be able to project radiation energy levels of 0-300 $mW/cm^2$ onto the inner surface of the device. The light for the optical fibers in the SARS is provided by an externally controllable and adjustable radiation source (e.g. different LEDs in one LED unit, different lasers, different lamp types). The external radiation source is controllable (i) in the radiated wavelength, (ii) in the radiation energy level and (iii) in the application time (length and sequence of the radiation impulses). Thus, control of the luminous power (radiation energy level per time unit) of the device is guaranteed by the external radiation source which controls the optical fibers. In addition, it is possible with this external light source to separately control specific groups of optical fibers and to thus individually illuminate certain areas of the SARS inner surface. It is thus possible to simultaneously provide different areas of the inside of the SARS with different wavelengths and different radiation energy levels (see FIG. 5F; different filling pattern represent areas illuminated by different wavelength).

The optical fibers and/or their ends can be arranged in different ways on the inside of the SARS (within the diffuser) (FIGS. 5G-5I).

Within the device, the feeding of substances and radiation is completely separate (optically opaque materials for the channels, possibly in addition mirrored optical fibers or normal optical fibers with total internal reflection, respectively) so that light-sensitive substances are not influenced and changed within the SARS through radiation. Substance feeding and the radiation unit are also controllable temporally separately through the external coupling devices.

FIGS. 5A-5I show schematic representations of possible arrangements of the optical fibers within the diffuser of the SARS. FIG. 5A shows a possible arrangement of few and relatively thick optical fibers within the diffuser for the forwarding of relatively high radiation energy levels (lateral view of the SARS, in this case the diffuser is depicted translucently). FIG. 5B shows the same arrangement of optical fibers as in A, but the diffuser is now diffusing light so that a more homogenous distribution of light is achieved. FIG. 5C shows the combination of radiation and substance application. FIG. 5D shows a possible arrangement of several thin optical fibers which can be controlled in groups within the diffuser (looking on the inside of the SARS, the diffuser is depicted translucently). FIG. 5E shows the same arrangement of the optical fibers as in A but the diffuser is now diffusing light so that a more homogeneous distribution of light is achieved. FIG. 5F shows the separate control of the grouped optical fibers through the external light source enables the simultaneous lighting of two areas with different wavelengths (represented as two different filling pattern). FIGS. 5G-5I depict different possible arrangements and distributions of the optical fibers within the diffuser. The optical fibers can have larger diameters and be restricted in number ( FIG. 5G) or can be very thin and relatively homogeneously distributed within the diffuser (FIG. 5H). Optical fibers can also be combined in groups which can then be controlled separately (FIG. 5I).

After opening the tissue connection between the orbital cavity and the bulb, the device of the invention is introduced into the Tenon's space. The device is placed on the equatorial and lateral part of the sclera, past the muscles. There, it is possible to apply substances or radiation during surgery without having to remove the device from the site to be treated (Advantages: (i) saves time during surgery, (ii) even or especially chosen distribution of substance application and radiation, (iii) less risk of damaging the surrounding tissue due to repeated insertion and removal of surgical instruments).

Figure 6:
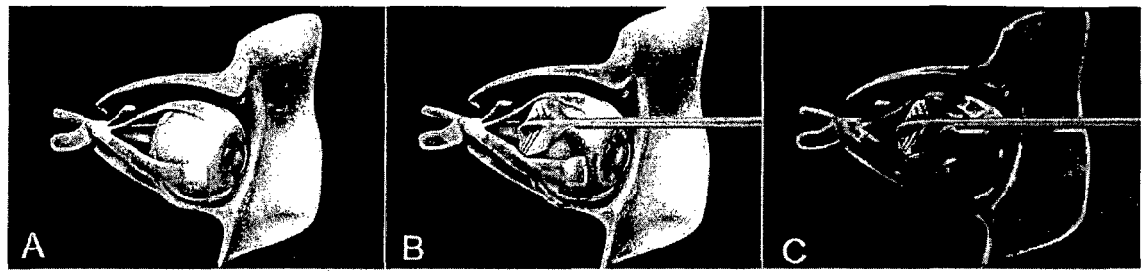
FIG. 6 shows a schematic representation of the anatomy of the eye (A), the positioning of the SARS in the Tenon's space of the orbital cavity (B), and of the SARS during treatment/radiation (C).

FIG. 6 shows a schematic representation of the anatomy of the eye (A), the positioning of the SARS in the Tenon's space of the orbital cavity (B) and of the SARS during treatment/radiation (C).

The device according to the invention can also be equipped with a temperature probe within the diffuser (inner part of the SARS). The feeding or the connection to the recording unit ensues in the same manner as the integration of the optical fibers in the diffuser.

The SARS can also be combined with a video surveillance system, wherein an endoscopic visualizing system is attached to/integrated into the SARS.

The present invention also relates to a method of treating the sclera in a subject comprising the steps of
  (i) placing of the disc/belt of the device of the invention into the Tenon's space in the eye of the subject so that the inner surface of the curved disc/belt is superficially in contact with a surface of an area of the sclera,
  (ii) applying an agent and/or electromagnetic radiation to the sclera of the subject.

Further, the invention pertains to a method of treating a pathological change or disease of the eye, comprising the steps of
  (i) placing of the disc/belt of the device of the invention into the Tenon's space in the eye of the subject so that the inner surface of the curved disc/belt is superficially in contact with a surface of an area of the sclera,
  (ii) applying an agent and/or electromagnetic radiation to the sclera of the subject.

In this context, the agent is preferably a chemical cross linker or a photosensitive substance. The photosensitive substance is for example riboflavin. Riboflavin can for example be applied followed by the application of light radiation.

The light radiation in the context of the devices and methods of the present invention is preferably UV-A light radiation (about 315 to about 380 nm, e.g. about 370 nm) or "blue light" radiation ("blue light" means that it has preferably a wavelength of from about 420 to about 480 nm, preferably about 425 to about 475 nm, more preferably about 450 to about 465 nm; preferred wavelengths are about 450 nm and about 465 nm), particularly when riboflavin is used as the photosensitive substance. When the light radiation is UV-A light radiation, the light intensity is for example in the range of 1 to 200 mW/cm$^2$, preferably 2 to 4 mW/cm$^2$ at the surface of the sclera. When the light radiation is "blue light" radiation, the light intensity may generally be higher than with UV-A radiation, for example it can be in the range of 1 to 350 mW/cm$^2$, preferably it is between 10 and 200 mW/cm$^2$, more preferably between 20 and 100 mW/cm$^2$, and even more preferably between 25 and 100 mW/cm$^2$ at the surface of the sclera. In general, when pulsed light is used higher light intensities may be used as compared to the application of continuous radiation. In certain embodiments, band pass filters may be used to create certain light profiles, e.g. 320 to 400 nm or 420 to 480 nm or 425 to 475 nm or 450 to 465 nm.

The pathological change or disease of the eye may in the context of the present invention for example be selected from the diseases and conditions discussed herein above and in particular selected from progressive myopia, scleritis, and pathological changes of the sclera such as tissue-macerating inflammation.

The invention also pertains to the device as described herein above for use in the treatment of a pathological change or disease of the eye.

Exemplary Procedure for Scleral Cross-linking Using the SARS Device

Aim of the surgical procedure is to cross link the collagen molecules in the scleral tissue of patient eyes by application of riboflavin as a photosensitizer and a combined irradiation with blue light. Riboflavin and/or the light irradiation (preferably both) are applied using the SARS device. Other photosensitizers and electromagnetic irradiation of another wavelength may also be used.

In the present procedure for the sclera cross linking (SXL) of human eyes, 0.01-20%, preferably 0.5% riboflavin in isotonic NaCl solution is applied to the surface of the entire sclera (or only areas which should be treated) for 5-60 minutes, preferably 30-40 minutes before the irradiation starts. The riboflavin solution might be pre-warmed (e.g. up to about 35° C.) before application, e.g. using a heated reservoir or a heating system in the device. The riboflavin solution may also be modified e.g. in terms of its viscosity or its tissue penetration behavior by adding dextran or another supplementary substance. The application of riboflavin may be repeated consecutively/alternately during the irradiation procedure or alternatively may only be applied in the beginning.

The irradiation power of blue light may be between about 1 to 350 mW/cm$^2$, preferably it is between 10 and 200 mW/cm$^2$, more preferably between 20 and 100 mW/cm$^2$, and even more preferably between 25 and 100 mW/cm$^2$ blue light power on the human scleral tissue. It is also possible to apply other electromagnetic wavelengths e.g. UV-light such as UV-A or a combination of two or more different wavelengths alternately or simultaneously during a treatment. Furthermore, it is possible to apply light of a certain bandwidth of electromagnetic wavelengths (e.g. blue light with a bandwidth from 420 to 480 nm; see above)

The scleral tissue can for example be irradiated approximately 20 min with an optimal blue light power (as discussed above) during the SXL operation. The irradiation time intervals may e.g. be 1-30 mm seconds, preferably 10-30 mm seconds with an interruption of e.g. 10 seconds to avoid any kind of thermic stress for the scleral tissue or can be continuous or pulsated in any way. Fresh riboflavin solution may be applied alternately e.g. every 5 minutes during the blue light irradiation to refresh the used riboflavin and additionally, to cool the irradiated scleral tissue. It may also be applied continuously. Other irradiation intervals and frequencies and prolonged or shortened irradiations procedures are feasible in dependence of the light power. This is a crucial advantage of the SARS device in comparison to other light sources: the position of the SARS need not be changed or retracted and repositioned during the entire irradiation procedure because riboflavin application is possible simultaneously. After SXL treatment the substance application and aspiration channel part of the SARS device can be used to remove excessive riboflavin and to flush the orbita with sterile isotonic NaCl solution. Additionally, this substance application and aspiration channel part of the SARS device can be used to flush the Tenon's spaces with a variety of flushing solutions. These solutions might contain pharmacologically active substances or molecules to support or stabilize the SXL treatment outcomes. E.g. fibroblasts may be activated as a response to the crosslinking treatment. The fibroblasts may e.g. change their morphology, intracellular ultrastructure and/or metabolism, and may increase in numbers. Changes of the collagen bundle and fibril structure (increased number of small size collagen fibrils) may be observed as a sign of remodelling of the collagen bundle structure. These remodelling processes might be supported by proliferation activity or migration of fibroblastst and changes of the gen and protein expression profile. Thus, it might be that matrix-metallo-proteinase (MMP) will be produced for the remodelling process of collagen and extracelluar matrix components. TIMPs are the regulatory proteins for the inhibition of MMP activities. Therefore, it is feasible that pharmacologically active substances are applied after the SXL treatment to modulate the activity of MMPs and/or TIMPs. Pharmacologically active substances applied via the SARS device can also modulate the activity of collagen producing gens or the naturally occurring collagen cross linking enzymes (e.g. lysyloxidase) or those substances can regulate the proliferation and migration of fibroblasts and other blood derived cells.

Exemplary Surgical Procedure of SXL in Human Patients

To perform surgery for scleral cross linking (SXL) anesthesia is mandatory. It might be any kind of local anesthesia by means of retrobulbar or parabulbar injection of anesthetics or a general anesthesia. Local anesthesia with a topical application of eye drops or the total omission of anesthesia is not recommended and is very unlikely. Preferably, a full anaesthesia is performed in combination with the application of a muscle relaxant. It might be necessary to inject additionally a retrobulbar block and/or to drop local anesthetics onto the eye. The entire surgical procedure (anesthesia, pre- and post-operative procedures and SXL) may take between 1 and 3 hours.

The SXL treatment is performed on a horizontally stabilized patient. Disinfection may e.g. be performed by applying Povidone-Iodine or any other disinfection solution with high care to the ciliary body and the conjunctiva. A common surgical cloth is used to cover the patient while the eye keeps accessible for operation.

It is possible to use indirect ophthalmoscopy, a yellow band pass filter and/or an operation micrsocope while performing surgery.

After disinfection a lid speculum will preferably be inserted under the lids to keep the lids wide open. An operation without using a lid speculum is feasible but not preferred. During the following steps artificial tears will be dropped onto the exposed parts of the eye (cornea, sclera and/or conjunctiva). After keeping the lids wide open by the speculum, the conjunctiva will be incised by a scalpel or a small scissors and the conjuctiva will be separated from the limbus. In cases of bleeding from small blood vessels the bleeding will be stopped (for instance by a heat treatment—cauterization) and the blood will be removed. A total incision of the conjunctiva around the entire eye (i.e. superior and inferior part of the lid/eye) and a complete separation of the conjunctiva from the limbus is recommended. It is also possible to reduce the dimension of the incision or in some cases it might only be necessary to open one part of the conjunctiva (superior or inferior). This depends on the shape and structure of the SARS device and the sclera area to be treated. The complete incision of the conjunctiva enables the access to the Tenon's space in the orbita. Now, the four straight eye muscles are looped by an insertion of a thread behind the muscles and that enables the manipulation and orientation of the eye. In some cases it might not be necessary to manipulate the eye muscles or the entire eye. This depends on the shape, structure and size of the SARS device which will be inserted. The SARS can consist of only one relatively small spoon-like applicator with a simple shape or of two, three, or four applicator parts with complex shapes adapted to the anatomy of the eye or the requirements of the patient and/or the pathology which has to be treated. The shape may also be adapted to the minimal required area to be treated. The various parts of the applicator can be introduced simultaneously into the Tenon's space around the eye bulbus or the treatment can be carried out consecutively. This depends on the scleral area which has to be treated. Simultaneous insertion of several parts of the SARS applicator reduces the operation time. Specifically adapted shapes of the SARS device avoid the undesirable cross-linking of muscles, larger blood vessels, surrounding tissue and the optic nerve. It is possible to customize the shape of the applicator for each patient to be treated.

After the insertion of the SARS device and its correct placement onto the bulbus the substance application starts and the sclera will be incubated with riboflavin e.g. for at least 20 minutes (as discussed above: various incubation periods and different concentrations and mixtures of riboflavin and other therapeutical substances are possible). It is possible to reduce the incubation time by adding other therapeutical substances.

After this pre-incubation the light irradiation starts (see above). During the irradiation period the riboflavin substance is applied alternately in a certain regime to refresh the used/bleached riboflavin. Used or excessive riboflavin can be aspirated by the SARS aspiration channels. Additionally, this substance application and aspiration part of the SARS device can be used to flush the Tenon's spaces with various flushing solutions (see above). After SXL treatment and an optional flushing period with various substances the SARS applicator/-s can be retracted from the orbita. Then the threads around the eye muscles should be removed and the conjunctiva has to be surgically closed by suturation. The treated patient eye may be medicated with topic antibiotics, antimycotics and/or steroid ointments or eye drops. In some cases this medical treatment is not mandatory. The eye may be taped and shielded by eye patches, eye ointment dressing and/or tamponade. After operation the patient should be kept under supervision of the anaesthesiologist and should be monitored by an ophthalmologist.

Other aspects, features, and advantages will be apparent from the description, including the figures and the claims.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

EXAMPLES

Example 1

Surgical Procedure in Rabbit Experiments

To perform the riboflavin/blue light collagen cross linking the animals were anesthetized by an intramuscular injection of ketamine hydrochlorid (50 mg/kg body weight weight; Ketamin 5%, Ratiopharm, Ulm, Germany) and xylazinhydrochlorid (10 mg/kg body weight; Rompun; Bayer Vital GmbH, Leverkusen, Germany). For maintenance of the anesthesia Ketamine hydrochlorid (25 mg/kg body weight) and xylazinhydrochlorid (5 mg/kg body weight) were injected intramuscular. Only the right eye underwent treatment whereas the contralateral untreated eye served as individual control. For avoiding corneal damage while surgery the left eye was treated with Floxal® eye ointment (Dr. Gerhard Mann GmbH, Berlin, Germany). Conjuncain was additionally used for local anesthesia of the right eye. After temporal canthotomy the conjunctiva was incised at the limbus to open the Tenon's space. Then Tenon's space was bluntly dissected in the superior temporal quadrant. The superior rectus muscle and the temporal rectus muscle were displayed and fixed by means of 5/0 Prolene sutures (Ethicon, Norstedt, Germany) to allow better exposition of the sclera and easier manipulation of the eye position during scleral treatment. Then riboflavin-5'-phosphate (Vitamin B2, 0.5% in PBS without any Dextran admixture, Streuli Pharma, Uznach, Switzerland) was dropped every five minutes on the exposed sclera to assure the plain penetration of riboflavin into the scleral stroma. After 20 minutes of soaking the temporal sclera was irradiated 20 min with one of the different intensities (10, 25, 50, 100, 200, 400 and 650 mW/cm$^2$) of blue light (450±25 nm) using a commercial dental light source (Bluephase 16i, Ivoclar Vivadent GmbH, Ellwangen-Jagst, Germany), matching one absorption maximum of riboflavin (450 nm). Here an irradiation of the cornea and the retina had to be avoided because of the destructive properties of blue light for the corneal and retinal tissue. Riboflavin drops were applied every 5 min during the entire irradiation period to avoid excessive photo-bleaching of the fluorophore. The adjustment of the applied light intensity (10 mW/cm$^2$ up to 400 mW/cm$^2$) was realized by custom built polypropylene spacing tubes and measured with a power meter in combination with a visible light sensor (LaserMate Q, Coherent Inc., Santa Clara, Calif., USA). A light intensity of 650 mW/cm$^2$ was realised by the light source without an additional spacing tube. After irradiation, the sutures were removed and the connective tissue was attached to the sclera using absorbable surgical sutures. Finally the canthothomy was readapted with absorbable surgical sutures. Both eyes were treated with Floxal® eye ointment (Dr. Gerhard Mann GmbH, Berlin, Germany) into the conjunctival fornix and the cornea avoiding infection and drying. The animals were monitored till awakening and kept in the Medizinisch-Experimentelles Zentrum of the University of Leipzig for 3 weeks.

Example 2

Measurement of Riboflavin Penetration in Scleral Tissue

Figure 7:
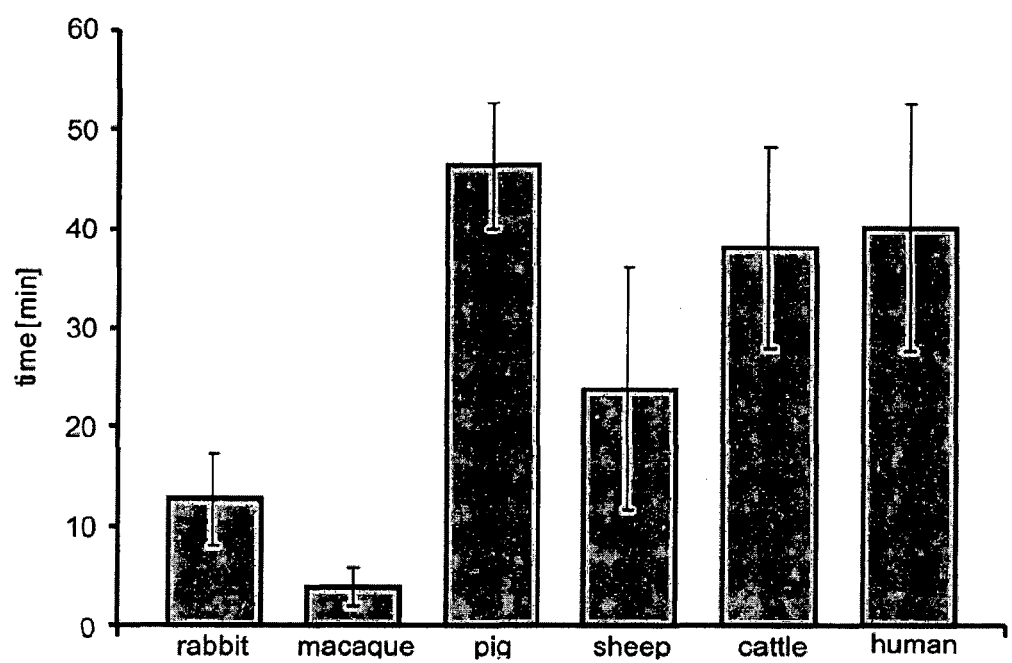
FIG. 7 shows the mean time period of the total tissue penetration of Riboflavin in scleral patches from various species.
Figure 8A:
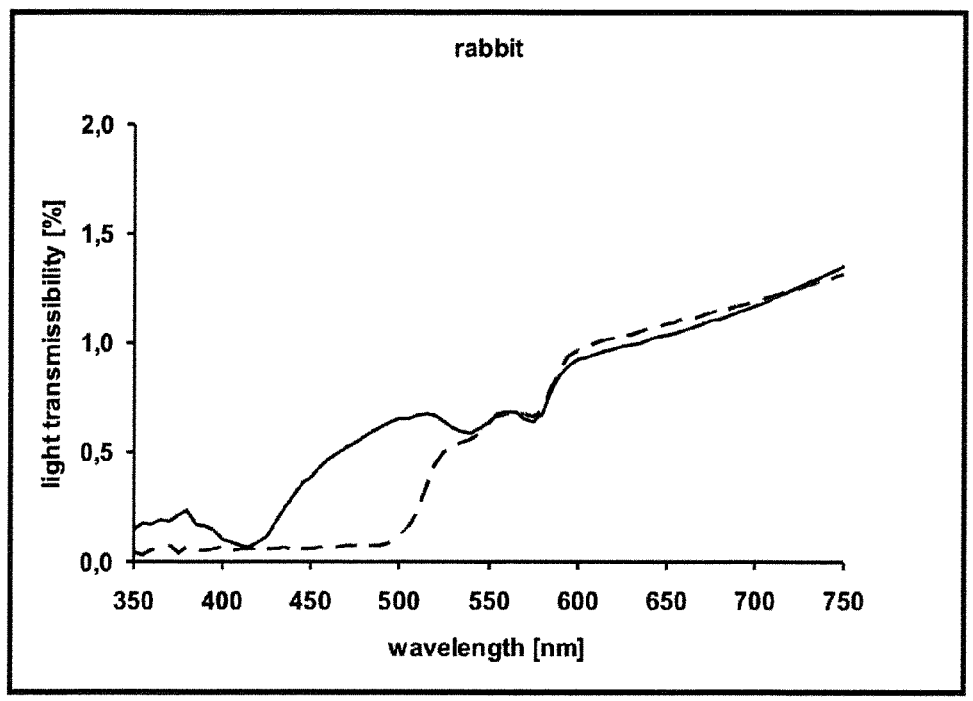
FIG. 8 demonstrates the spectral light transmissibility characteristics of scleral tissue from various species.
Figure 8B:
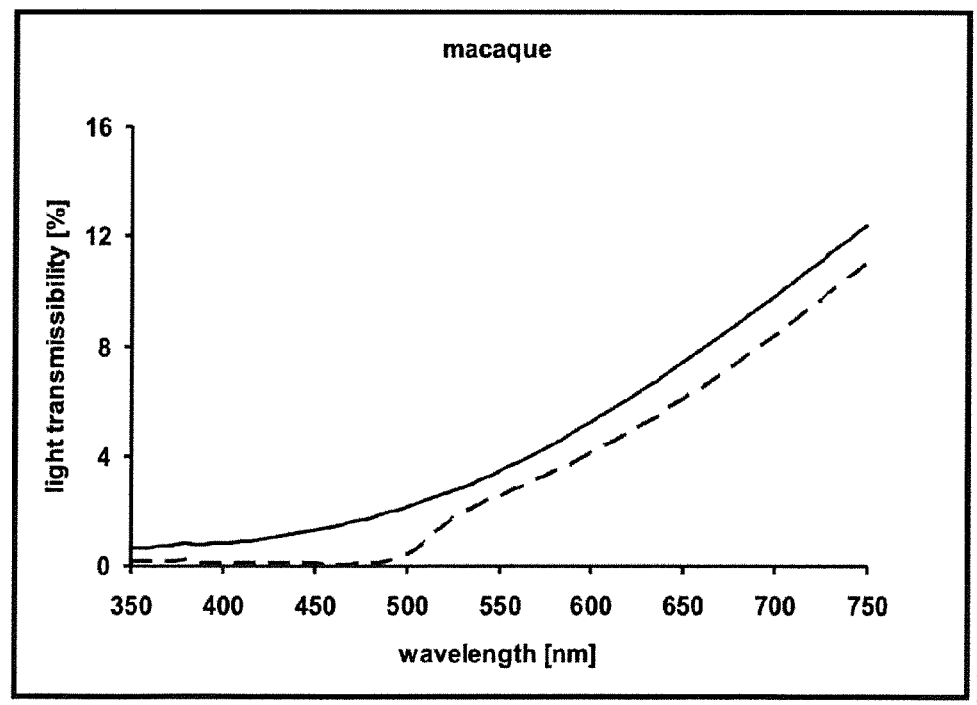
Figure 8C:
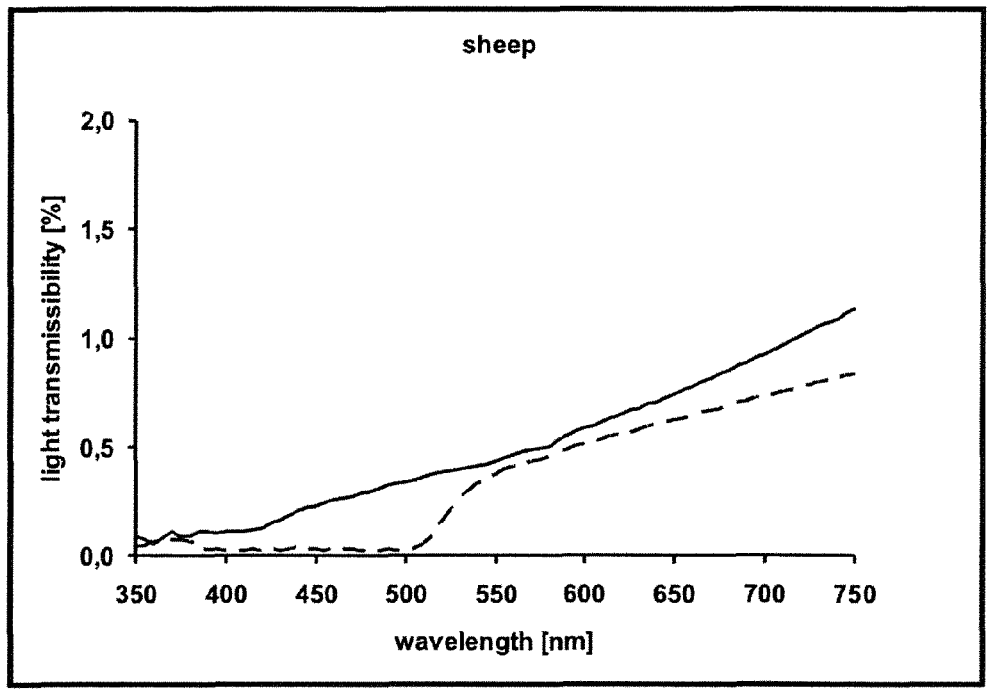
Figure 8D:
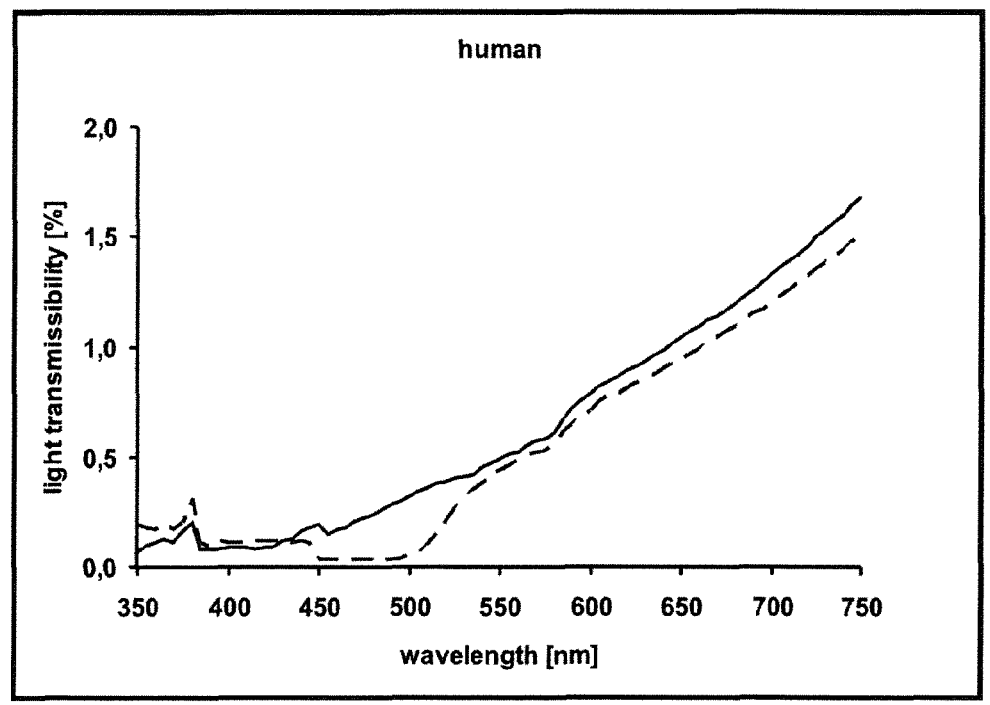

FIG. 7 displays the mean time period of the total tissue penetration of Riboflavin in scleral patches from various species. The penetration time was calculated by an application of riboflavin onto one side of a scleral tissue patch and the total appearance on the opposite side monitored as a maximum of fluorescence by a fluorescence microscope. Compared to 10-20 minutes in rabbit sclera, it takes approximately 30-40 minutes for riboflavin to penetrate the human sclera. Frozen/thawed scleral tissue was used for this examination; however, the results were similar with freshly isolated (i.e. non-frozen) tissue.

FIG. 8 demonstrates the spectral light transmissibility characteristics of scleral tissue from various species. Approximately only 0.5-1% of the light (up to 500 nm wavelength) penetrates the scleral tissue of all species. The application of riboflavin reduces the transmissibility further at wavelength up to 530 nm caused by the strong light absorption of Riboflavin at that wavelengths.

Figure 9:
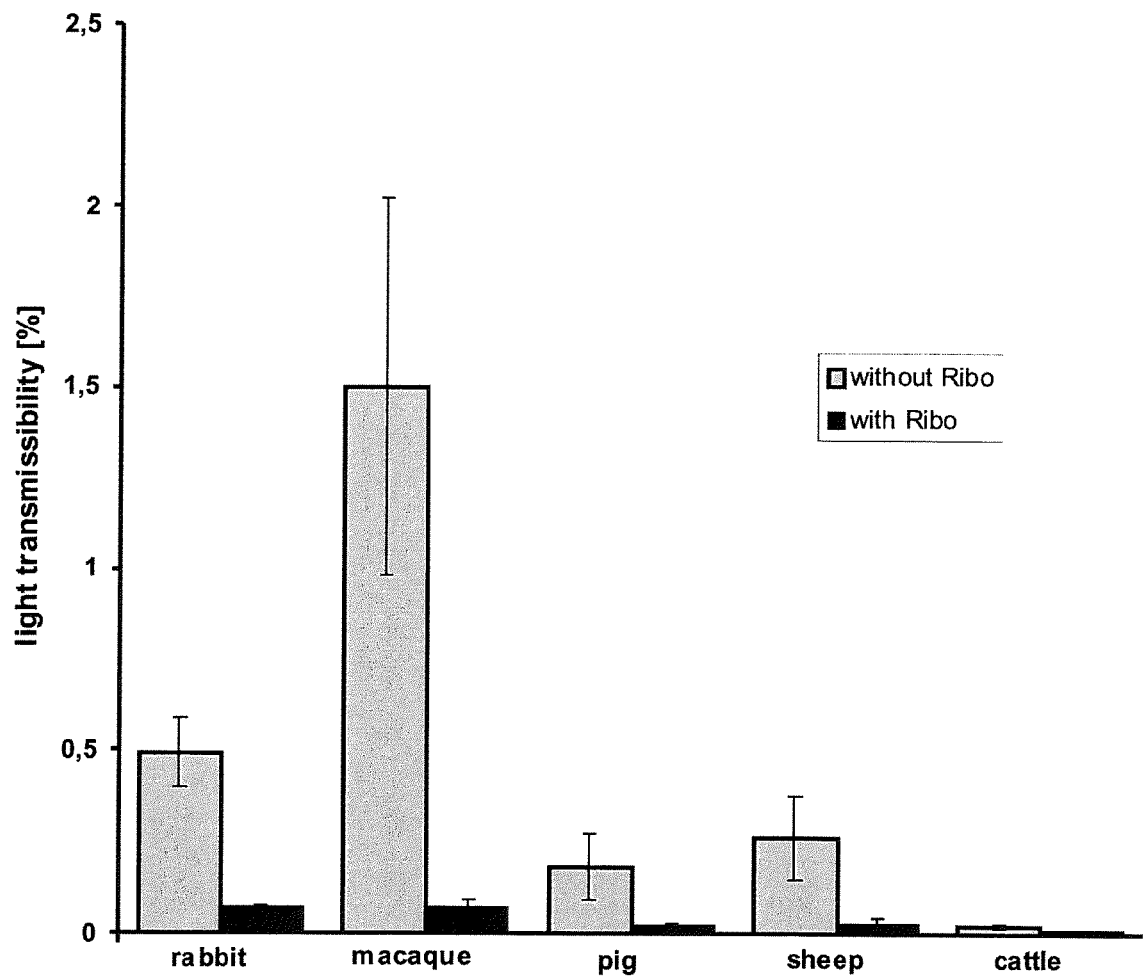
FIG. 9 shows the light transmissibility characteristics of freshly isolated scleral tissue from various species at a wavelength of 450 nm.

FIG. 9 demonstrates the light transmissibility characteristics of freshly isolated scleral tissue from various species at a wavelength of 450 nm. Approximately only 0.5% of the light penetrates the scleral tissue of all species. The application of riboflavin ("Ribo") reduces the transmissibility further at 450 nm caused by the strong light absorption of riboflavin at that wavelength.

Example 3

Results of Sclera Cross-linking in Different Species

Figure 10:
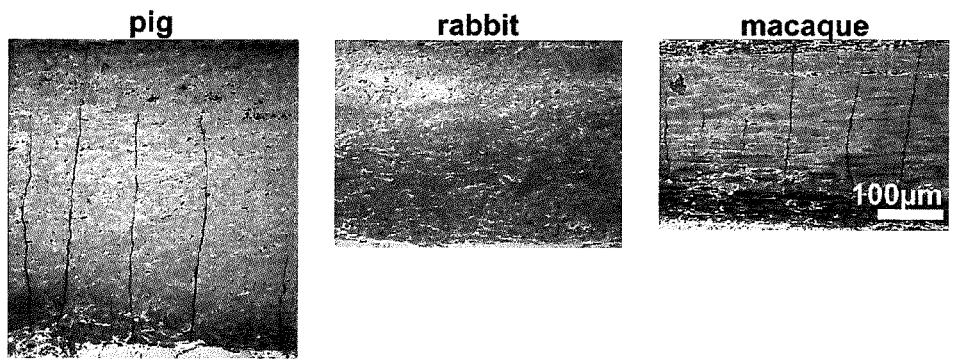
FIG. 10 shows light microscopy images of histological semi-thin sections (0.5 µm thickness, Toluidin blue staining) to compare the dimensions and structure of scleral tissue from various species.
Figure 10:
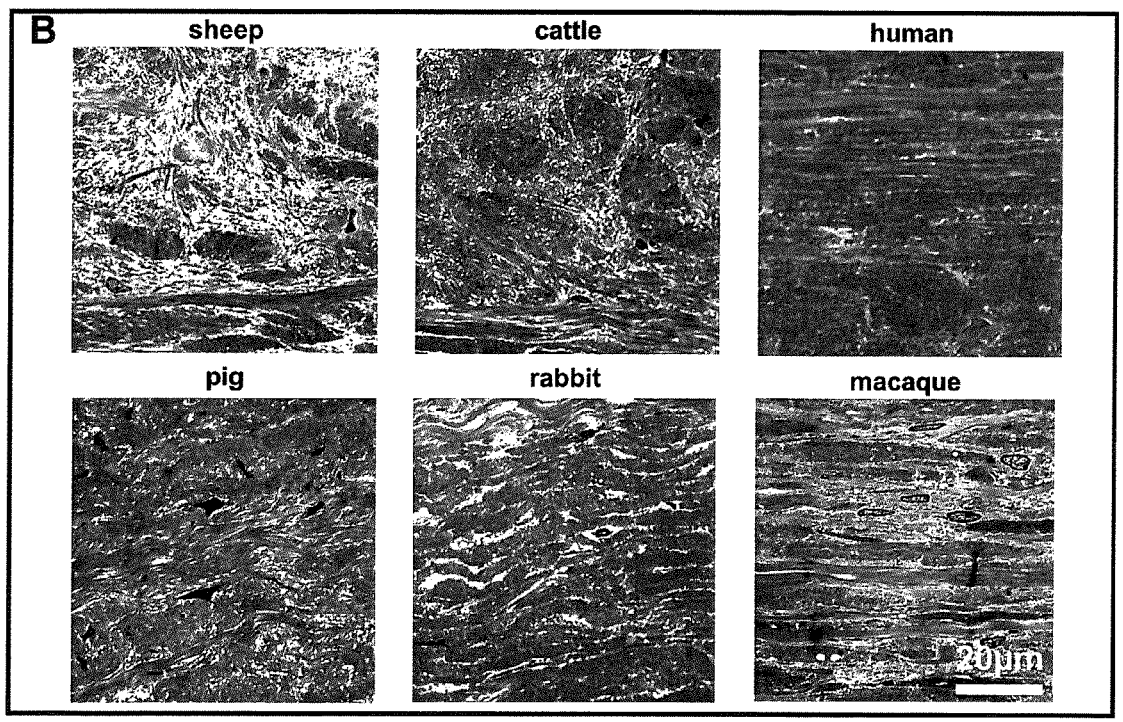

FIG. 10: Light microscopy of histological semi-thin sections (0.5 μm thickness, Toluidin blue staining) to compare the dimensions and structure of scleral tissue from various species. The scale bar in A (macaque) sclera is valid for all scleral sections in A and demonstrates the differences of thickness in the posterior part of the sclera. B shows histological sections at higher magnification to reveal structural differences. The histological examinations revealed large structural similarities between rabbit and human sclera and differences in comparison to other species. The scale bar in B (macaque) sclera is valid for all scleral sections in B.

Figure 11:
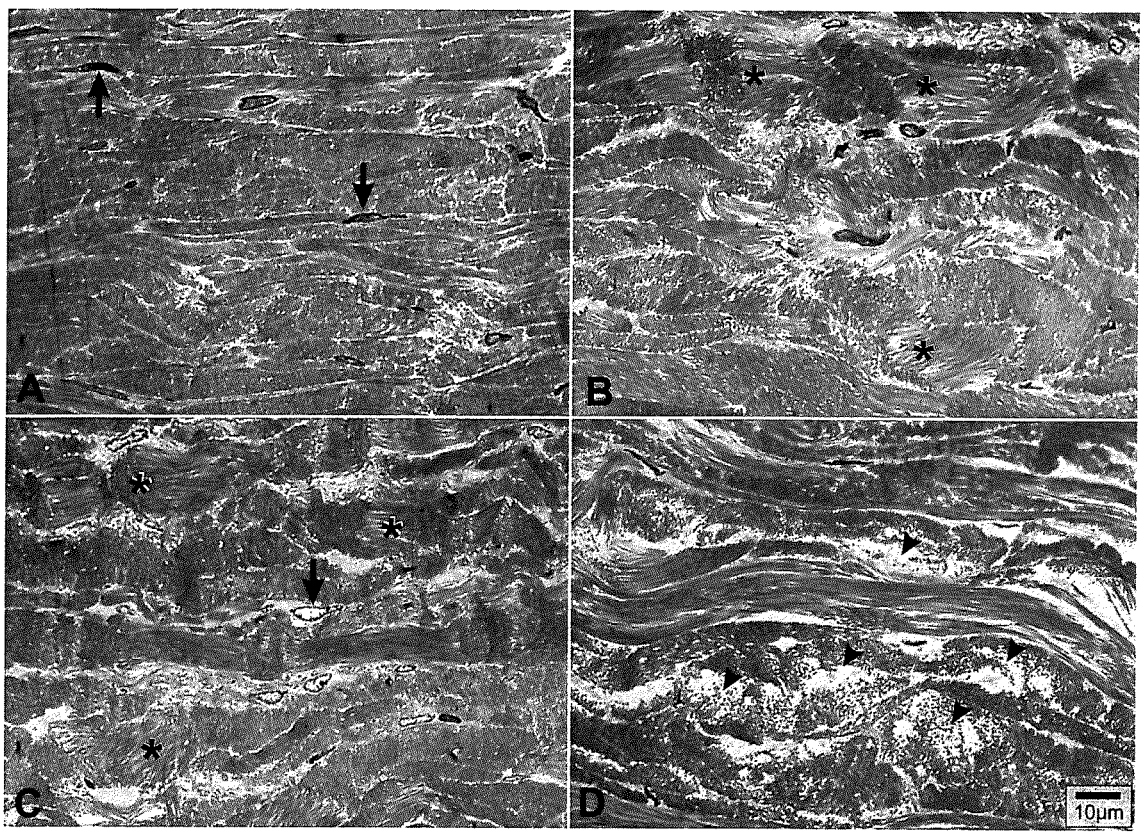
FIG. 11 shows microphotographs demonstrating the comparison of morphological properties of acute isolated (A) and frozen/thawed (B-D) scleral tissue with (C and D) and without (A and B) crosslinking treatment.

FIG. 11: Comparison of morphological properties of acute isolated (A) and frozen/thawed (B-D) scleral tissue with (C and D) and without (A and B) cross linking treatment. Microphotographs display histological semithin sections of scleral tissue visualized by light microscopy (Toluidin blue staining). A: Acute isolated non-treated scleral tissue is characterized by a very compact collagen bundle arrangement and spindle-like ellipsoid cell bodies of fibroblasts (arrows) between the collagen bundles. B: Thawed (former frozen for storage) scleral tissue show a loosen bundle structure and contorted bundles (asterisks) in comparison to acute isolated scleral tissue. C: No dramatic changes of the overall structure of (thawed) scleral tissue were obvious after cross linking treatment with riboflavin and 25 mW/cm$^2$ compared to the untreated thawed tissue in B. Cell bodies of fibroblasts appear swollen (arrow) and the bundle structure is contorted (asterisks). D: After a cross linking treatment with riboflavin and blue light of 200 mW/cm$^2$ the bundle structures loosen further and the collagen bundles appear strongly contorted. The inter-bundle and inter-fibril space increases (arrow heads) and many collagen fibrils appear separated. Scale bar in D is valid for A-D.

Figure 12:
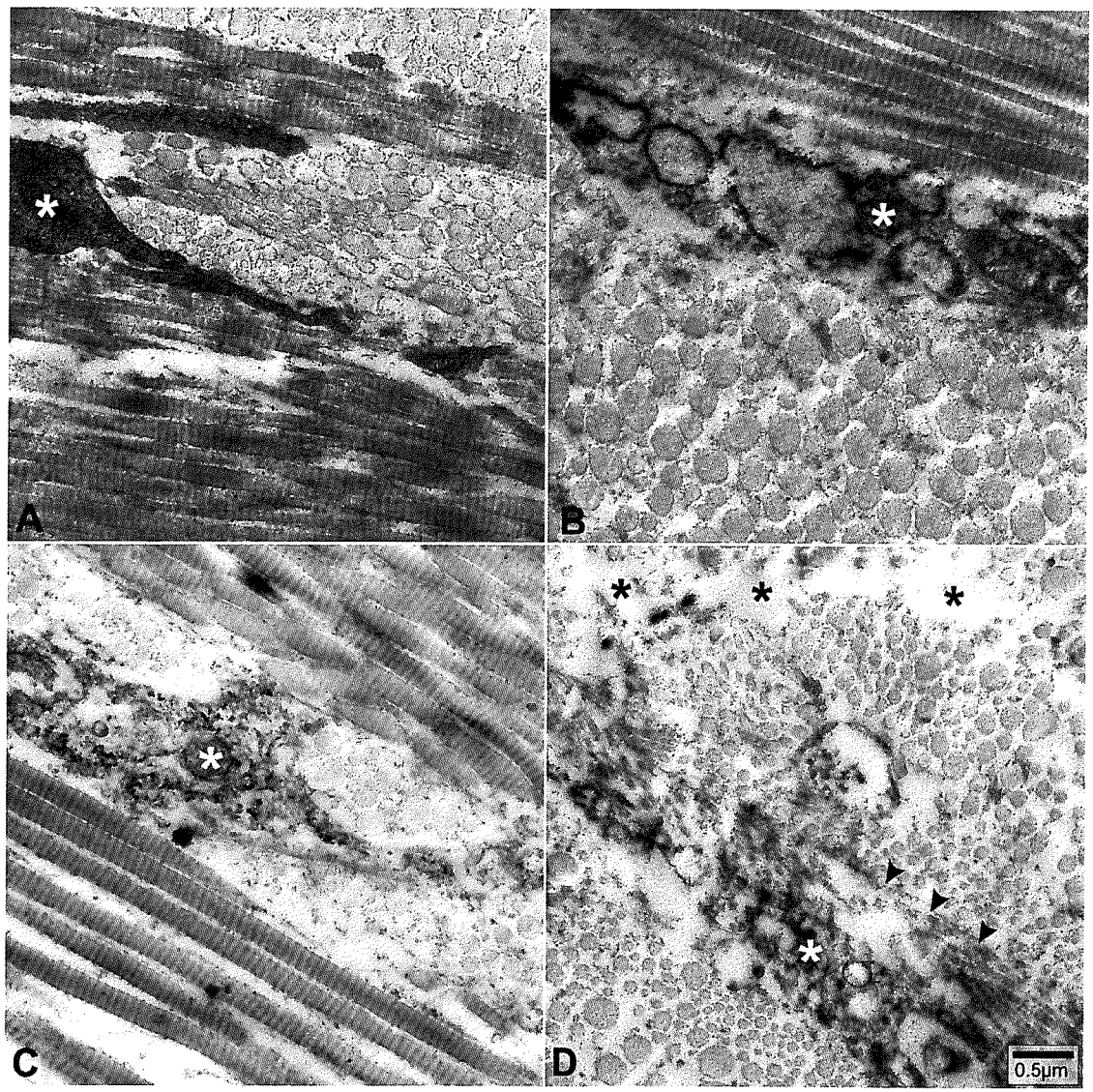
FIG. 12 shows electron microscopic microphotographs of acute isolated (A) and frozen/thawed (B-D) scleral tissue with (C and D) and without (A and B) crosslinking treatment.

FIG. 12: Electron microscopic microphotographs of acute isolated (A) and frozen/thawed (B-D) scleral tissue with (C and D) and without (A and B) cross linking treatment. A: Acute isolated non-treated scleral tissue is characterized by a very compact collagen bundle arrangement with different orientations (cross and transverse sections of the bundles are visible). Spindle-like electron dense cell bodies of fibroblasts (asterisk) with tiny cell processes are located between the collagen bundles and sub-cellular structures are well defined and intact. B: As a consequence of storage at −20° C. and thawing fibroblasts (asterisk) of the scleral tissue are swollen and show disrupted cellular structures and cell membranes. Collagen fibrils seem to be intact and are often still organized compactly in bundles. C: After cross linking treatment with riboflavin and 25 mW/cm$^2$ scleral fibroblasts show similar disrupted appearance as in untreated thawed tissue shown in B. The collagen fibre structure itself appears intact. D: After cross linking treatment with riboflavin and blue light of 200 mW/cm$^2$ the collagen bundle structures appear slightly loosened and the few collagen fibril arrangements appear disrupted (arrow heads). Occasionally, the inter-fibril space increases (black asterisks) and cellular structures (white asterisk) appear destroyed. Scale bar in D is valid for A-D.

The invention claimed is:

1. A device for a medical treatment of a sclera, the device comprising a curved disc, wherein:
   the disc is configured to be placed into the Tenon's space;
   the disc is formed such that an inner surface of the curved disc is superficially contactable to a surface of an area of the sclera so as to superficially cover said area; and
   the disc comprises two, three, four, or more independent channel systems, wherein at least part of the channel systems are configured as agent channel systems such that the channels of each of the agent channel systems are tubes adapted to lead an agent from a proximal end of the tube to a distal opening, and wherein at least part of the channel systems are configured as optical guiding systems, wherein each of the optical guiding systems is adapted to guide electromagnetic waves from the proximal end of a first channel to the distal openings of the optical guiding system,
   wherein the disc comprises a base layer made from a material that is sterilisable and/or heat-resistant, and is impervious to light, wherein the disc comprises one or more additional layers, wherein the base layer and the one or more additional layers are arranged as stacked layers with the base layer on an outer side of the disc so as to support the one or more additional layers, and wherein at least one of the one or more additional layers is a diffuser adapted for diffusing electromagnetic waves, and wherein at least part of the distal openings of at least part of the optical guiding systems are arranged within or at the outer side of the additional layer(s) being a diffuser.

2. The device of claim 1, wherein the disc has the form of an elongate bowl.

3. The device of claim 1, wherein one or more recesses are formed in an edge of the disc, wherein the one or more recesses are positioned and formed such that the recesses leave free space for eye muscles, blood vessels and/or nerves when the disc is positioned on said area of the sclera.

4. The device of claim 1, wherein each of the channel systems comprises a first channel having a proximal end on an edge of the disc or extending beyond the edge of the disc, wherein the first channel at the distal end either splits into two or more second channels or has a distal opening, wherein each of the second channels at the distal end again either can split into two or more third channels or has a distal opening, and wherein the splitting of the channels can be further repeated such that each of the channels either splits into two or more channels or has a distal opening.

5. The device of claim 4, wherein at least part of the distal openings being arranged on a treatment site facing surface of a layer of the disc are formed as elongate openings, wherein, an elongate opening may be formed such that part of the channel having the elongate opening is shaped as a half-cylinder with its round side being embedded in the respective layer and being open in the direction pointing away from the respective layer.

6. The device of claim 4, wherein:
the channels systems are embedded in the base layer, wherein each of the openings at a distal end of a channel is arranged on the inner surface of the base layer.

7. The device of claim 4, wherein the channels of the optical guiding system(s) comprise one or more bundles of optical conductors, and wherein at each split of a channel, the bundle comprised in the channel is fanned out into a number of smaller bundles, the number of smaller bundles corresponding to the number of the two or more subsequent channels, such that each of the two or more subsequent channels comprises one of the smaller bundles.

8. The device of claim 4, wherein (i) a handle is arranged at the edge of the disc and the handle is arranged as a tube and the first channel of each of the channel systems extends through the handle, and/or (ii) wherein a handle is connectable with the edge of the disc, and the handle is arranged as a tube and the first channel of each of the channel systems can be conducted through the handle.

9. The device of claim 1, wherein the distal openings of at least a part of the channel systems are regularly, irregularly or distinctly distributed with respect to a plane of the disc, wherein the plane of the disc has different areas having different distributions of the openings.

10. The device of claim 1, wherein the density of the distal openings of at least a part of the channel systems is variable with respect to a plane of the disc.

11. The device of claim 1, wherein the disc has a symmetric shape, and the distal openings of at least a part of the channel systems are arranged symmetrically in accordance with the symmetry of the disc.

12. The device of claim 1, wherein the channels of at least part of the agent channel systems are at least partly isolated against electromagnetic radiation.

13. The device of claim 12, wherein the channels of at least part of the agent channel systems are isolated against electromagnetic radiation with a wavelength in the range between 100 nm and 2000 nm.

14. The device of claim 1, wherein the inner surface of the disc has a structure adapted to allow for an improved distribution of the agent when the agent is led through the agent channel system(s), and wherein the surface structure comprises chamfers, or elements selected from the group consisting of bars, half-spheres, pyramids and cones.

15. The device of claim 1, wherein at least one of the one or more additional layers can be made of a sponge or a sponge-like material or a porous material that is sterilisable and/or heat-resistant, and wherein at least part of the distal openings of at least part of the agent channel systems are arranged within or at the outer side of the layer(s) made from a sponge or a sponge-like material or a porous material.

16. The device of claim 1, wherein the device comprises two, three, four, or more independent optical guiding systems, and wherein each of the optical guiding systems is adapted for guiding a range of electromagnetic radiation, and, wherein the proximal end of the first channel of each of the optical guiding systems is connectable to a source of electromagnetic radiation.

17. The device of claim 16, wherein the proximal end of the first channel of each of the optical guiding systems is connectable to a source of electromagnetic radiation such that each of the optical guiding systems can be supplied independently with electromagnetic radiation.

18. The device of claim 1, wherein at least one of the channel systems is configured as a cleaning system such that the channels of the cleaning system are tubes adapted to lead an agent, and wherein distal openings of each of the cleaning system(s) are arranged on the outer surface of the disc and/or on the edge of the disc.

19. The device of claim 18, wherein:
at least one of the cleaning system(s) is configured as a suction system, wherein a proximal end of a first channel of each of the suction system(s) is connectable to a pump means, and wherein at least one cleaning system is configured as a flushing system configured to deliver one or more agents to the distal openings, wherein the suction system(s) and the flushing system(s) are identical cleaning system(s) adapted for suction and flushing in an alternative manner, or
wherein at least one cleaning system is configured as suction system and at least one further cleaning system is configured as flushing system.

20. The device of claim 1, wherein (i) a handle is arranged at the edge of the disc, and/or (ii) wherein a handle is connectable with the edge of the disc.

21. The device of claim 1, further comprising one or more sensor(s) or measurement system(s).

22. The device of claim 21, wherein the at least one or more of the sensor(s) or measurement system(s) is selected from the group consisting of a temperature sensor, a camera system, a biomechanical sensor, and/or a pH meter.

23. The device of claim 21, wherein the at least one or more of the sensor(s) or measurement system(s) comprises a pressure sensor.

24. The device of claim 1, wherein the disc has the form of a spherical cap.

25. The device of claim 1, wherein the disc has the form of an elongate bowl having a length between 10 mm and 30 mm and a width between 5 mm and 25 mm.

26. The device of claim 1, wherein the disc has the form of an elongate bowl having a length between 15 mm and 25 mm and a width between 10 mm and 15 mm.

27. The device of claim 1, wherein the thickness of the disc is lower than or equal to 5 mm, and has a minimum of 2 mm.

28. The device of claim 1, wherein the thickness of the disc is lower than or equal to 3 mm, and has a minimum of 2 mm.

29. The device of claim 1, wherein each of the one or more additional layers is made from a plastic or a metal material that is a light-diffusing, impervious to light and/or sponge like material.

30. The device of claim 1, wherein:
the channel systems are at least partly embedded in the base layer and/or at least partly embedded in one or more of the additional layers, wherein each of the openings at a distal end of a channel is arranged on the inner surface of the base layer or within one of the additional layers or on the surface of one of the additional layers.

31. A method of treating the sclera in a subject comprising the steps of
(i) placing of the disc of the device of claim 1 into the Tenon's space in the eye of the subject so that the inner surface of the curved disc is superficially in contact with a surface of an area of the sclera,
(ii) simultaneously or alternately applying an agent and electromagnetic radiation to the sclera of the subject.

32. A method of treating a pathological change or disease of the eye, comprising the steps of
(i) placing of the disc of the device of claim 1 into the Tenon's space in the eye of the subject so that the inner surface of the curved disc is superficially in contact with a surface of an area of the sclera,
(ii) simultaneously or alternately applying an agent and electromagnetic radiation to the sclera of the subject.

* * * * *